US008381726B2

(12) United States Patent
Turiello

(10) Patent No.: US 8,381,726 B2
(45) **Date of Patent: *Feb. 26, 2013**

(54) SAFETY SYSTEM AND METHOD OF AN UNDERGROUND MINE

(75) Inventor: Anthony J Turiello, Portola Valley, CA (US)

(73) Assignee: Rescue Air Systems, Inc., San Carlos, CA (US)

( * ) Notice: Subject to any disclaimer, the term of this patent is extended or adjusted under 35 U.S.C. 154(b) by 389 days.

This patent is subject to a terminal disclaimer.

(21) Appl. No.: 12/690,943

(22) Filed: Jan. 21, 2010

(65) Prior Publication Data

US 2011/0030838 A1 Feb. 10, 2011

Related U.S. Application Data

(63) Continuation-in-part of application No. 11/505,525, filed on Aug. 16, 2006, now Pat. No. 7,677,247.

(51) Int. Cl.
*A61G 10/00* (2006.01)
*A61M 16/00* (2006.01)
*E04D 13/18* (2006.01)

(52) U.S. Cl. ......... 128/205.26; 128/203.27; 128/204.18; 128/204.21; 128/200.24; 52/173.3

(58) Field of Classification Search ............. 128/200.24, 128/201.24, 203.27, 204.18, 204.21, 205.26, 128/897, 898; 707/101; 52/169.6, 173.3; 454/169–172; 137/377, 382
See application file for complete search history.

(56) References Cited

U.S. PATENT DOCUMENTS

| | | | | |
|---|---|---|---|---|
| 2,299,793 | A * | 10/1942 | Cannaday et al. | 128/202.13 |
| 4,862,931 | A * | 9/1989 | Vella | 141/1 |
| 5,570,685 | A * | 11/1996 | Turiello | 128/202.13 |
| 6,688,309 | B2 * | 2/2004 | York | 128/205.22 |
| 7,168,428 | B1 * | 1/2007 | Zoha | 128/202.27 |
| 7,527,056 | B2 * | 5/2009 | Turiello | 128/205.26 |
| 7,621,269 | B2 * | 11/2009 | Turiello | 128/204.21 |
| 7,673,629 | B2 * | 3/2010 | Turiello | 128/204.21 |
| 7,677,247 | B2 * | 3/2010 | Turiello | 128/205.26 |
| 7,694,678 | B2 * | 4/2010 | Turiello | 128/204.21 |
| 7,762,289 | B2 * | 7/2010 | McCulloh et al. | 141/2 |

OTHER PUBLICATIONS

National Fire Protection Association; National Fire Protection Association Standards on Self Contained Breathing Apparatus for Fire Fighters 1981 Edition; May 19, 1981; Dallas, Texas, USA.*

* cited by examiner

*Primary Examiner* — Annette Dixon
(74) *Attorney, Agent, or Firm* — Raj Abhyanker, P.C.

(57) ABSTRACT

Disclosed are a safety system and method of an underground mine. In one embodiment, a method of safety of a mine structure includes expediting an air extraction process from an emergency support system by including a RIC (rapid interventions company/crew)/UAC (universal air connection) fitting to a fill panel to fill a breathable air apparatus. The method may include ensuring that a prescribed pressure of the emergency support system maintains within a threshold range of the prescribed pressure by including a valve of the emergency support system to prevent leakage of breathable air from the emergency support system. The method may also include maintaining the prescribed pressure of the emergency support system such that a system pressure is compatible with a breathable air apparatus through a distribution structure that is rated for use with compressed air.

23 Claims, 18 Drawing Sheets

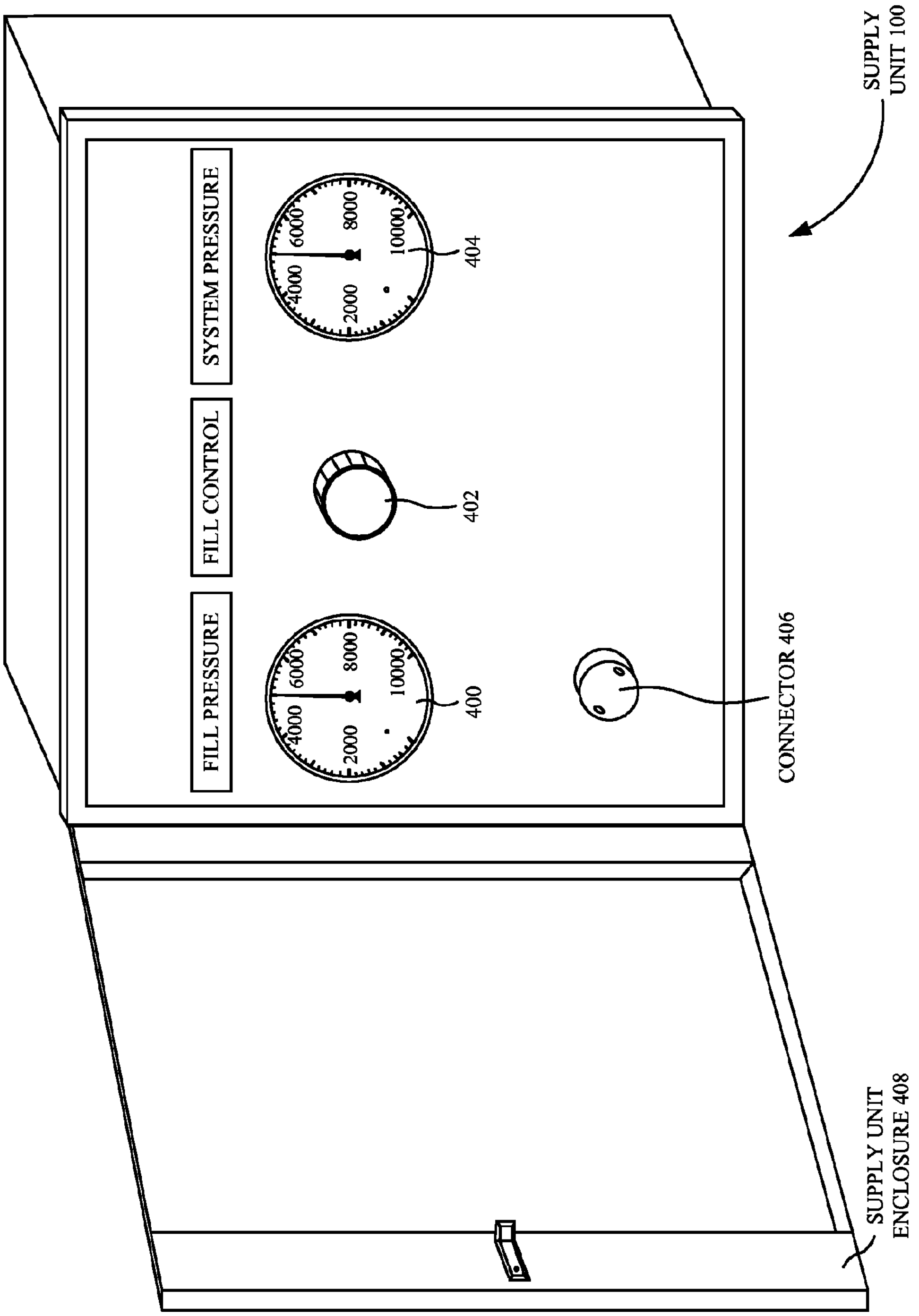
FIGURE 4A (FRONT VIEW)

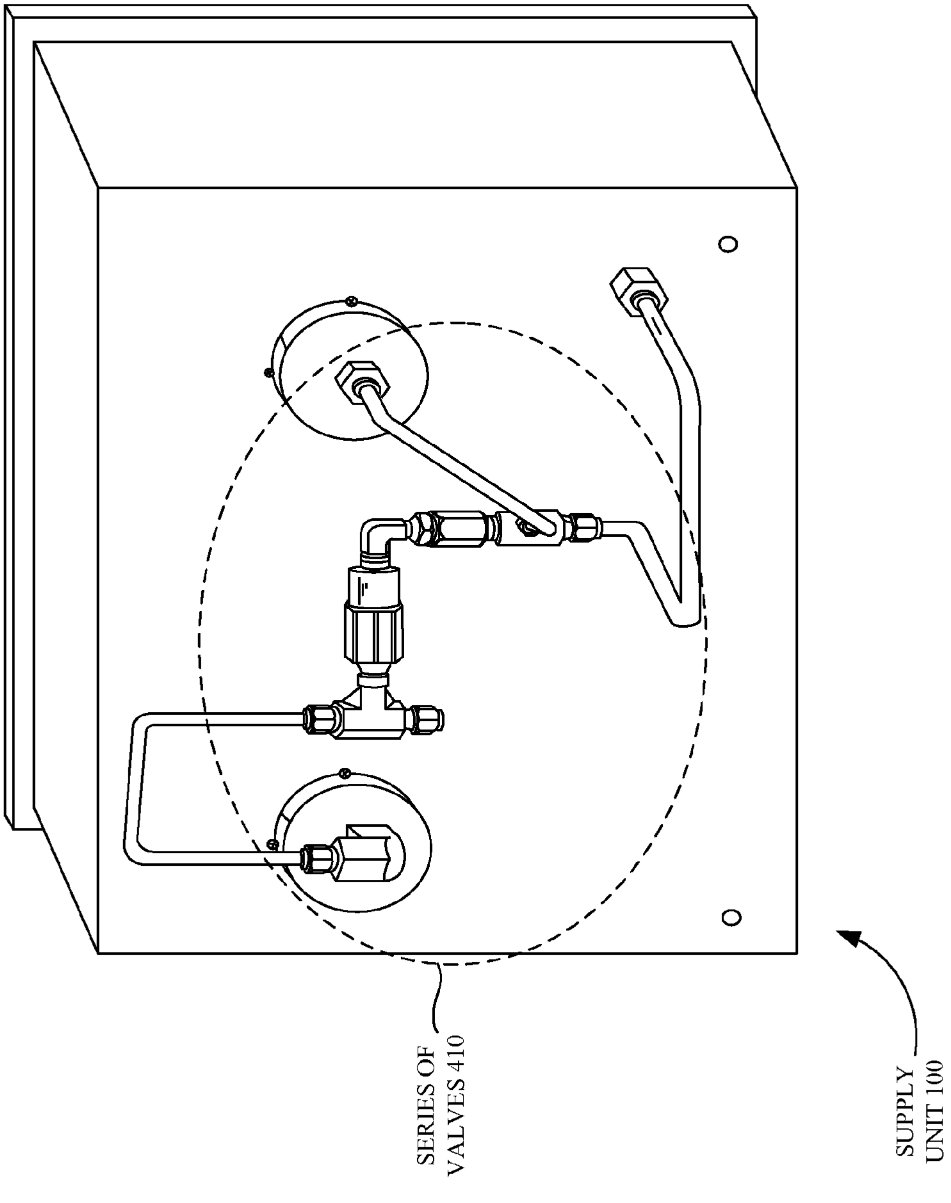
FIGURE 4B (REAR VIEW)

SAFETY SYSTEM AND METHOD OF AN UNDERGROUND MINE

CLAIM OF PRIORITY

This is a Continuation-in-part application and claims priority from:

U.S. application No. 11/505,525 now U.S. Pat. No. 7,677,247 B2 titled "SAFETY SYSTEM AND METHOD OF AN UNDERGROUND MINE" filed on Aug. 16, 2006.

FIELD OF TECHNOLOGY

This disclosure relates generally to the technical fields of safety systems and, in one example embodiment, to a safety system and method of an underground mine.

BACKGROUND

In a mine, providing and maintaining adequate safety may be of importance. For example, serious or fatal accidents occurring in underground mine in the United States over the years may have resulted from an inability to control the roof of the mine. For example, a fatal accident can occur from the falling of even one large rock from the roof of the mine.

In a case of an emergency situation of the mine, emergency personnel may be deployed on-site of the mine to alleviate the emergency situation through mitigating a source of hazard as well as rescuing stranded individuals from the mine. The emergency situation may include events such as a building fire, a chemical attack, tenor attack, subway accident, underground mine collapse, and/or a biological agent attack.

In such situations, breathing air inside the mine may be hazardously affected (e.g., depleted, absorbed, and/or contaminated). In addition, flow of fresh air into the underground may be significantly hindered due to the mine having enclosed regions, lack of windows, and/or high concentration of contaminants. As a result, inhaling air in the mine may be extremely detrimental and may further result in death (e.g., within minutes). Furthermore, emergency work may often need to be performed from within the mine (e.g., due to a limitation of emergency equipment able to be transported on a ground level).

The emergency personnel's ability to alleviate the emergency in an efficient manner may be significantly limited by the lack of breathing air and/or the abundance of contaminated air. A survival rate of stranded civilians in the structure may substantially decrease due to a propagation of contaminated air throughout the mine placing a large number of innocent lives at significant risk.

As such, the emergency personnel may utilize a portable breathing air apparatus (e.g., self-contained breathing apparatus) as a source of breathing air during a rescue mission. However, the portable breathing air apparatus may be heavy (e.g., 20-30 pounds) and may only provide breathing air for a short while (e.g., approximately 15-30 minutes). In the emergency situation, the emergency personnel may need to walk and/or climb to a particular location within the mine to perform rescuing work due to inoperable transport systems (e.g., obstructed walkway, elevators, moving sidewalks, and/or escalators, etc.). As such, by the time the emergency personnel reaches the particular location, his/her portable breathing air apparatus may have already depleted and may require running back to the ground floor for a new portable breathing air apparatus. As a result, precious lives may be lost due to time being lost.

SUMMARY

Disclosed are a safety system and method of an underground mine. In one aspect, a method of safety of a mine structure includes expediting an air extraction process from an emergency support system by including a RIC (rapid interventions company/crew)/UAC (universal air connection) fitting to a fill panel to fill a breathable air apparatus. The method may include ensuring that a prescribed pressure of the emergency support system maintains within a threshold range of the prescribed pressure by including a valve of the emergency support system to prevent leakage of breathable air from the emergency support system. In addition, the method also includes maintaining the prescribed pressure of the emergency support system such that a system pressure is compatible with a breathable air apparatus through a distribution structure that is rated for use with compressed air that couples a supply unit and the fill panel to transfer breathable air of a source of compressed air to the fill panel. The method may also include pressurizing breathable air to facilitate a flow of breathable air from the emergency support system to the breathable air apparatus. The method may further include pressurizing breathable air to increase the flow of breathable air to decrease an amount of time required to fill the breathable air apparatus.

In another aspect, a method of safety of a mine structure includes facilitating a flow of air from an emergency support system by including a RIC/UAC fitting to a fill location to fill a breathable air apparatus. The method may include pressurizing breathable air to increase the flow of breathable air to decrease an amount of time required to fill the breathable air apparatus. In addition, the method may include connecting a RIC/UAC fitting to a fill station to provide an additional source of breathable air. The fill location may be a site in the structure providing access to a RIC/UAC fitting coupled to the emergency support system. The method may further include adjusting a fill pressure to ensure that the fill pressure of the source of compressed air does not exceed the prescribed pressure of the emergency support system through a pressure regulator of the supply unit.

In yet another aspect, a method of safety of a mine structure includes extracting breathable air from an emergency support system by including a RIC/UAC fitting to a fill location to fill a breathable air apparatus. The method may include pressurizing the breathable air in the emergency support system to a first pressure greater than a pressure rating of the breathable air apparatus. In addition, the method may include adjusting a second pressure of the RIC/UAC fitting by including a valve of the emergency support system to match with a threshold range the pressure rating of the breathable air apparatus. The method may also include suspending transfer of breathable air from the source of compressed air to the emergency support system through utilizing a valve of the supply unit when necessary. The method may further include preventing leakage of air from the emergency support system potentially leading to pressure loss of the emergency support system through utilizing a valve of the fill panel.

In a further aspect, a method of safety of a mine structure includes safeguarding a filling process of a breathable air apparatus by enclosing the breathable air apparatus in a secure chamber of a fill site of the emergency support system of the building structure to provide a safe placement to supply the breathable air to the breathable air apparatus. The method may include ensuring that a prescribed pressure of the emergency support system maintains within a threshold range of the prescribed pressure by including a valve of the emergency support system to prevent leakage of breathable air from the emergency support system. In addition, the method may include maintaining the prescribed pressure of the emergency support system such that a system pressure is compatible with a breathable air apparatus through a distribution structure that is rated for use with compressed air that couples a supply unit and the fill site to transfer breathable air of a source of compressed air to the fill site. The method may also include securing the breathable air apparatus to prevent the breathable air apparatus from injuring a user of the breathable air apparatus during the filling process of a breathable air apparatus. The method may further include securing the breathable air apparatus to ensure that the breathable air apparatus has access to air during the filling process.

In yet further aspect, a method of safety of a mine structure includes safeguarding a filling process of a breathable air apparatus by enclosing the breathable air apparatus in a secure device of a fill site of the emergency support system of the building structure to provide a safe placement to supply the breathable air to the breathable air apparatus. The method may include securing the breathable air apparatus to prevent the breathable air apparatus from injuring a user of the breathable air apparatus during the filling process of a breathable air apparatus. In addition, the method may include securing the breathable air apparatus to ensure that the breathable air apparatus has access to air during the filling process. The secure device may prevent the escape of the breathable air apparatus in case the breathable air apparatus is damaged during the filling process of the breathable air apparatus. The method may also include adjusting a fill pressure to ensure that the fill pressure of the source of compressed air does not exceed the prescribed pressure of the emergency support system through a pressure regulator of the supply unit.

The methods disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE VIEWS OF DRAWINGS

Example embodiments are illustrated by way of example and not limitation in the figures of accompanying drawings, in which like references indicate similar elements and in which:

FIG. 4A is a front view of a supply unit, according to one embodiment.

FIG. 4B is a rear view of the supply unit, according to one embodiment.

Figure 1:
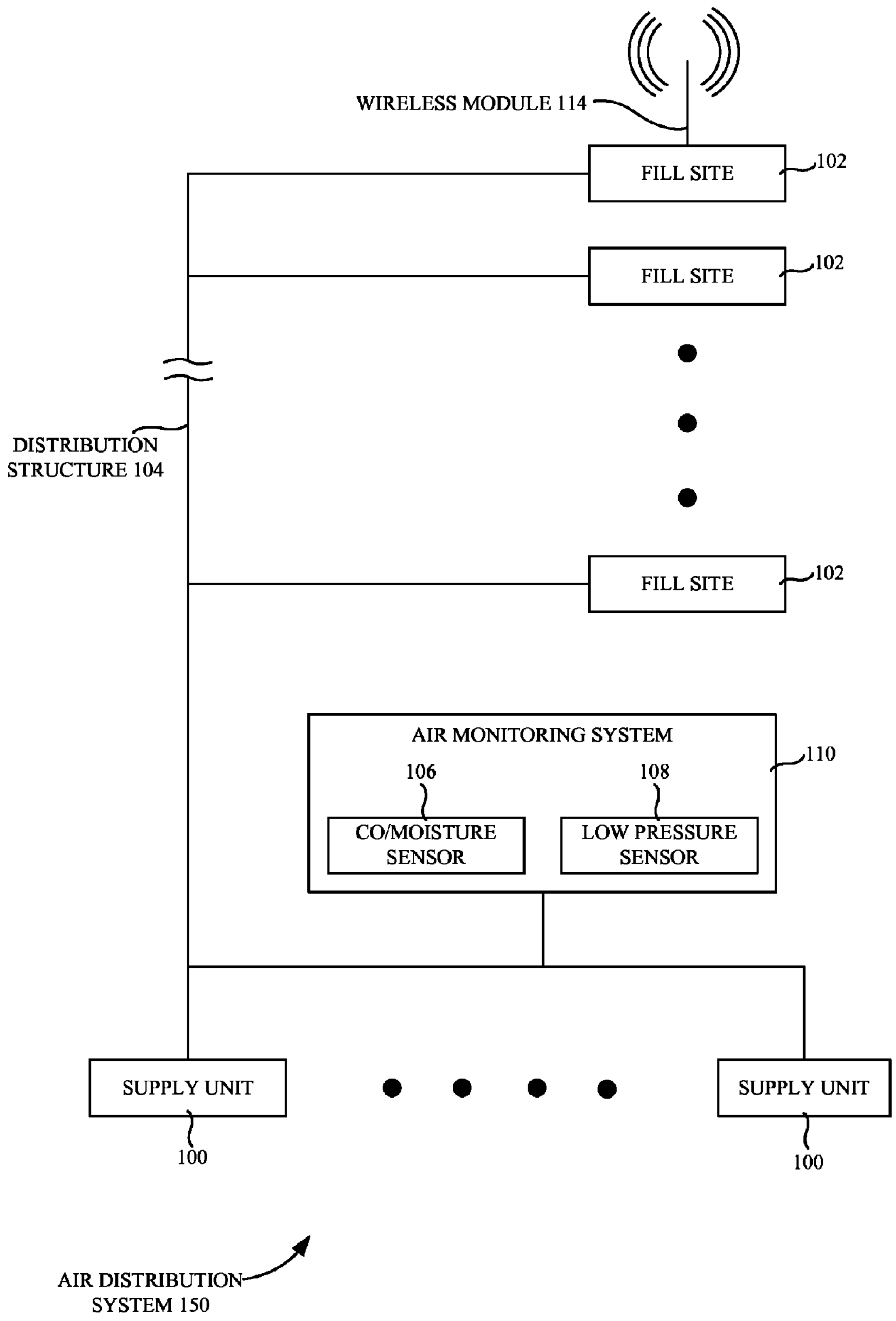
FIG. 1 is a schematic view of an air distribution system in a building structure, according to one embodiment.

Other features of the present embodiments will be apparent from accompanying Drawings and from the Detailed Description that follows.

DETAILED DESCRIPTION

Example embodiments, as described below, may be used to provide a safety system and method of an underground mine. Although the present embodiments have been described with reference to specific example embodiments, it will be evident that various modifications and changes may be made to these embodiments without departing from the broader spirit and scope of the various embodiments.

A municipality code may be a body of law written by a governmental body, such as a city, state, and/or federal government. The municipality code may be authored or merely adopted by a municipality. It may be enforced by the municipality or another governmental body. According to Merriam-Webster, a municipality may be a primarily urban political unit having corporate status and usually powers of self-government.

An authority having jurisdiction (AHJ) may be a governmental agency or sub-agency which regulates a construction process. A governmental agency may be the municipality in which the building is located. However, construction performed for supra-municipal authorities may be regulated directly by the owning authority, which may be the AHJ.

Some national and regional governments may issue model codes, such as a model building code. The model codes issued by the national and regional government may be used by as a baseline for to author codes for a state or a province. The codes may be adopted by a municipality as a locally enforceable code.

Types of locally enforceable codes may include building codes and fire codes. A building code may be enforced by building inspectors from a municipal building department. A fire code may be enforced by local fire prevention officers from a local fire department.

A building code may be a set of rules that specify the minimum acceptable level of safety for constructed objects such as buildings and non-building structures (such as bridges, tunnels, or parking structures). A purpose of the building codes may be to protect public health, safety and general welfare as they relate to a construction and occupancy of buildings and structures. The building code becomes law of a particular jurisdiction when formally enacted by the appropriate authority.

The fire code (also fire prevention code or fire safety code) may be a model code adopted by the state or local jurisdiction and enforced by fire prevention officers within municipal fire departments. It may be a set of rules prescribing minimum requirements to prevent fire and explosion hazards arising from storage, handling, or use of dangerous materials, or from other specific hazardous conditions. It complements the building code. The fire code may be aimed at preventing fires, ensuring that necessary training and equipment will be on hand, and that the original design basis of the building, including the basic plan set out by the architect, is not compromised. The fire code may also address inspection and maintenance requirements of various fire protection equipments in order to maintain optimal active fire protection and passive fire protection measures.

A fire safety code may include administrative sections about the rule-making and enforcement process, and substantive sections dealing with fire suppression equipment, particular hazards such as containers and transportation for combustible materials, and specific rules for hazardous occupancies, industrial processes, and/or exhibitions.

Sections may establish the requirements for obtaining permits and specific precautions required to remain in compliance with a permit. For example, a fireworks exhibition may require an application to be filed by a licensed pyrotechnician, providing the information necessary for the issuing authority to determine whether safety requirements can be met. Once a permit is issued, the same authority (or another delegated authority) may inspect the site and monitor safety during the exhibition, with the power to halt operations, when unapproved practices are seen or when unforeseen hazards arise. Embodiments described herein may use the safety codes described above.

FIG. 1 is a diagram of an air distribution system 150 in a building structure, according to one embodiment. The air distribution system 150 may include any number of supply unit 100, any number of fill site 102 (e.g., a fill panel and/or a fill station, etc.) that are coupled to the rest of the air distribution system 150 through a distribution structure 104. The air distribution system 150 may also include an air monitoring system 110 having a CO/Moisture sensor 106 and a pressure sensor 108. The supply unit 100 may be placed at a number of locations exterior to the building structure (e.g., a horizontal building structure such as a shopping mall, IKEA®, Home Depot®, a vertical building structure such as a high rise building, a mid rise building, and/or a low rise building, a mine, a subway, and/or a tunnel, etc.) to allow ease of access by a source of compressed air and/or to expedite supplying the air distribution system 150 with breathable air. The supply unit 100 described herein may also include a valve that may be used for suspending transfer of breathable air from the source of compressed air to the emergency support system when required. The supply unit 100 may also be placed at locations that are substantially free of traffic (e.g., parked cars, vehicle movement, and/or human traffic, etc.) to decrease potential obstruction that may be present in an emergency situation (e.g., a building fire, a chemical attack, tenor attack, subway accident, mine collapse, and/or a biological agent attack, etc.).

The fill site 102 may also be placed at a number of locations of the building structure (e.g., a horizontal building structure such as a shopping mall, IKEA®, Home Depot®, a vertical building structure such as a high rise building, a mid rise building, and/or a low rise building, a mine, a subway, and/or a tunnel, etc.) to provide multiple access points to breathable air in the building structure. The building structure may have any number of fill site 102 (e.g., a fill panel and/or a fill station, etc.) on each floor and/or have any number of fill site 102 (e.g., a fill panel and/or a fill station, etc.) on different floors. Each fill site 102 may be sequentially coupled to one another and to the supply unit 100 through the distribution structure 104. The distribution structure 104 may include any number of pipes to expand an air carrying capacity of the air distribution system 150 such that breathable air may be replenished at a higher rate. In addition, the fill site 102 may include wireless capabilities (e.g., a wireless module 114) for communication with remote entities (e.g., the supply unit 100, building administration, and/or an authority agency, etc.). The system described herein may enable an emergency personnel to extract air (e.g., refill air, etc.) from the fill site 102A-N at a rapid pace. Therefore, the fill site 102A-N described herein may be designed for expediting an air extraction. Connectors, structures in the system described, may include an RIC (rapid interventions company/crew)/UAC (universal air connection) to enable expedition of an air extraction process.

The air monitoring system 110 may include multiple sensors such as the CO/moisture sensor 106 and the pressure sensor 108 to track air quality of the breathable air in the air distribution system 150. Since emergency personnel (e.g., a fire fighter, a SWAT team, a law enforcer, and/or a medical worker, etc.) depend on the breathable air distributed via the air distribution system 150, it is crucial that air quality of the breathable air be constantly maintained. The air monitoring system 110 may also include other sensors that detect other hazardous substances (e.g., benzene, acetamide, acrylic acid, asbestos, mercury, phosphorous, propylene oxide, etc.) that may contaminate the breathable air.

In one embodiment, the distribution structure 104 may be compatible with use with compressed air facilitates dissemination of the breathable air of the source of compressed air to multiple locations of the building structure. A fire rated material may encase the distribution structure 104 such that the distribution structure has the ability to withstand elevated temperatures for a period of time. The pipes of the distribution structure 104 may include a sleeve exterior to the fire rated material to further protect the fire rated material from any damage. Both ends of the sleeve may be fitted with a fire rated material that is approved by an authority agency. In addition, the distribution structure 104 may include a robust solid casing to prevent physical damage to the distribution structure potentially compromising the safety and integrity of the air distribution system.

The distribution structure 104 may include support structures at intervals no larger than five feet to provide adequate structural support for each pipe of the distribution structure 104. The pipes and the fittings of the distribution structure 104 may include any of a stainless steel and a thermoplastic material that is compatible for use with compressed air.

In another embodiment, the air distribution system may include an air monitoring system (e.g., the air monitoring system 110) to automatically track and record any impurities and contaminants in the breathable air of the air distribution system. The air monitoring system (e.g., the air monitoring system 110) may have an automatic shut down feature to suspend air distribution to the fill site 102 in a case that any of an impurity and contaminant concentration exceeds a safety threshold. For example, a pressure monitoring system (e.g., the pressure sensor 108) may automatically track and record the system pressure of the air distribution system. Further, a pressure switch may be electrically coupled to an alarm system such that the fire alarm system is set off when the system pressure of the air distribution system is outside a safety range. In one or more embodiments, a valve may be included in the system of the emergency support system to prevent leakage of breathable air from the emergency support system. In addition, the valve may ensure that a prescribed pressure of the emergency support system maintains within a threshold range of the prescribed pressure (e.g., as recommended by safety procedures). In addition, the system described herein may be configured to maintain the prescribed pressure of the emergency support system such that a system pressure is compatible with a breathable air apparatus through a distribution structure that is rated (e.g., based on a prescribed code) for use with compressed air that couples the supply unit 100 and the fill panel to transfer breathable air of a source of compressed air to the fill panel.

Also, in one or more embodiments, there may be different levels of pressuring the breathable air. The pressure may be prescribed as per safety norms. According to one embodiment, the breathable air in the emergency support system may be pressurized to a pressure (e.g., first pressure) greater than a pressure rating of the breathable air apparatus. In addition, a second pressure may be adjusted using the RIC/UAC fitting by including a valve of the emergency support system to match with a threshold range the pressure rating of the breathable air apparatus.

Figure 2:
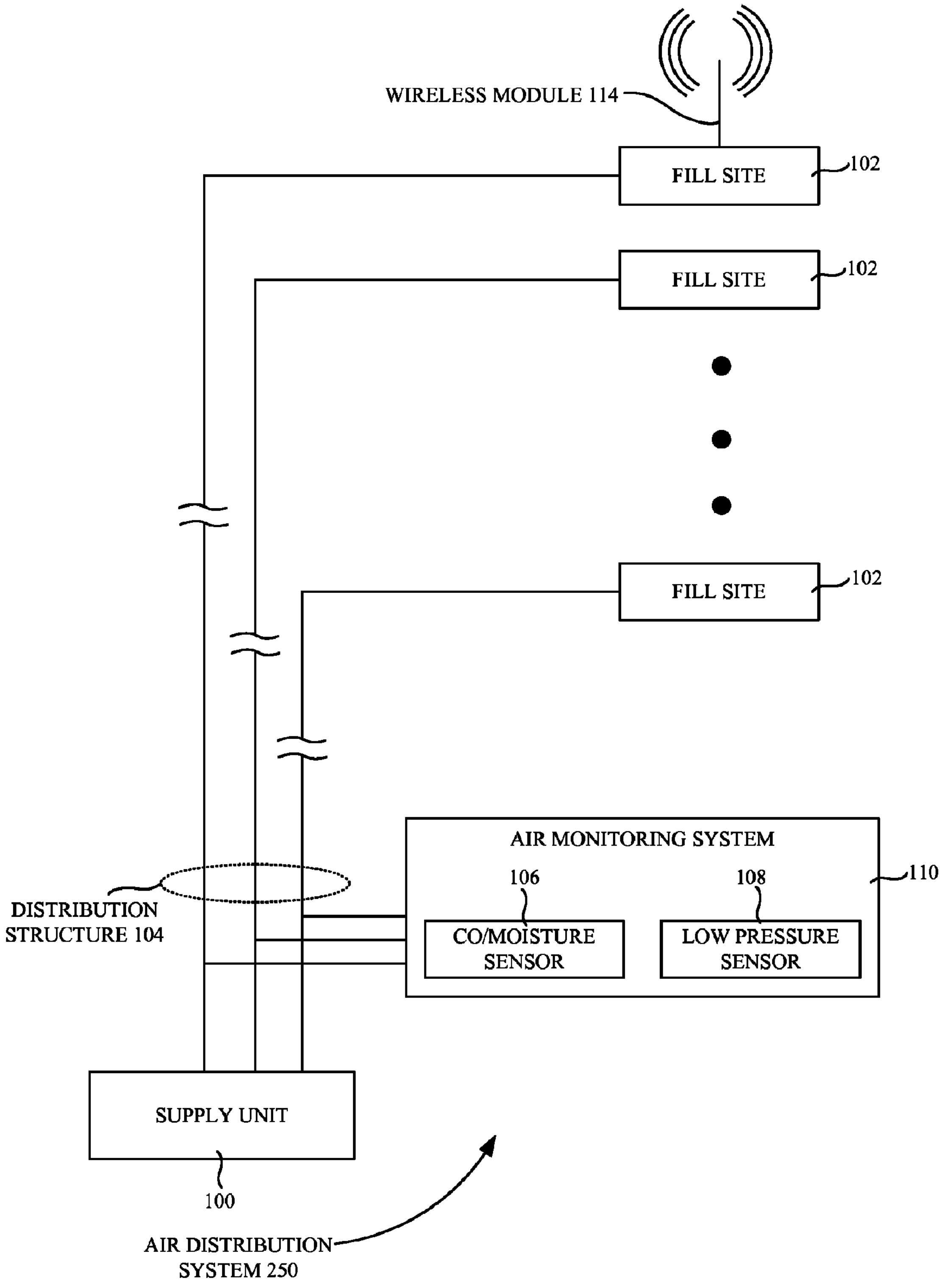
FIG. 2 is another schematic view of the air distribution system in the building structure, according to one embodiment.

FIG. 2 is another diagram of an air distribution system 250 in a building structure, according to one embodiment. The air distribution system 250 may include any number of supply unit 100, any number of fill site 102 (e.g., a fill panel and/or a fill Station, etc.) that are coupled to the rest of the air distribution system 150 through a distribution structure 104. The air distribution system 150 may also include the air monitoring system 110 having a CO/Moisture sensor 106 and a pressure sensor 108. In the air distribution system 250, the distribution structure 104 may individually couple each fill site 102 (e.g., a fill panel and/or a fill station, etc.) to a supply unit 100. Individual coupling may be advantageous in that in the case one pipe of the distribution structure 104 becomes inoperable the other pipes can still deliver air to the fill site 102 (e.g., a fill panel and/or a fill station, etc.). The other system components (e.g., the fill site 102, the supply unit 100, and the air monitoring system 110 were described in detail in the previous section).

Figure 3:
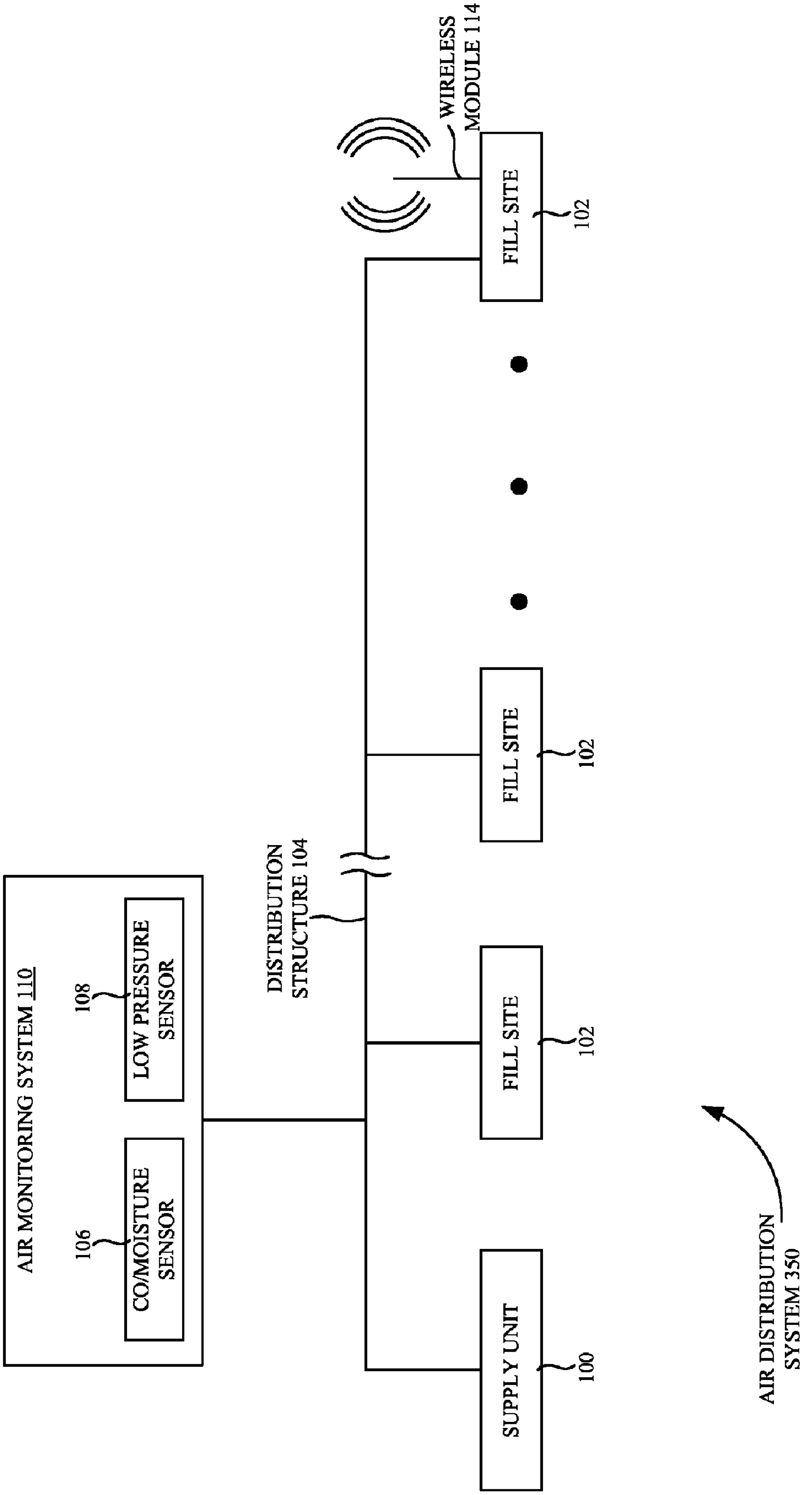
FIG. 3 is schematic view of the air distribution system in the building structure having fill sites located horizontally from one another, according to one embodiment.

FIG. 3 is a diagram of an air distribution system 350 in a building structure having any number of fill site 102 (e.g., a fill panel and/or a fill station, etc.) located horizontally from one another, according to one embodiment.

The air distribution system 350 may include any number of supply unit 100, any number of fill site 102 (e.g., a fill panel and/or a fill station, etc.) that are coupled to the rest of the air distribution system 150 through a distribution structure 104. The air distribution system 150 may also include the air monitoring system 110 having a CO/Moisture sensor 106 and a pressure sensor 108. In the air distribution system 250, the distribution structure 104 may sequentially couple each fill site 102 (e.g., a fill panel and/or a fill station, etc.) displaced predominantly horizontally from a supply unit 100. Each air distribution system (e.g., the air distribution system 150, 250, 350) may be used in conjunction with one another depending on the particular architectural style of the building structure in a manner that provides most efficient access to the breathable air of the air distribution system reliably. The other system components (e.g., the fill site 102, the supply unit 100, and the air monitoring system 110 were described in detail in the previous section).

FIG. 4A is a front view of a supply unit 100, according to one embodiment. The supply unit 100 provides accessibility of a source of compressed air to supply air to an air distribution system (e.g., an air distribution system 150, 250, and/or 350). The supply unit may include a fill pressure indicator 400, a fill control knob 402, a system pressure indicator 404, and/or a connector 406. The fill pressure indicator 400 may indicate the pressure level at which breathable air is being delivered by the source of compressed air to the air distribution system (e.g., an air distribution system 150, 250, and/or 350 of FIGS. 1-3). In one or more embodiments, the breathable air may be pressurized to facilitate a flow of breathable air from the system (e.g., the emergency support system) to the breathable air apparatus. The emergency personnel (e.g., fire fighters, etc.) may require quick refill of the breathable air apparatus. In addition, the time required for refilling the breathable air apparatus should be low in order to save time. Therefore, the breathable air may be pressurized to increase the flow of breathable air to decrease an amount of time required to fill the breathable air apparatus.

The system pressure indicator 404 may indicate the current pressure level of the breathable air in the air distribution system. The fill control knob 402 may be used to control the fill pressure such that the fill pressure does not exceed a safety threshold that the air distribution system is designed for. The connector 406 may be a CGA connector that is compatible with an air outlet of the source of compressed air of various emergency agencies (e.g., fire station, law enforcement agency, medical provider, and/or SWAT team, etc.). The connector 406 of the supply unit 100 may facilitate a connection with the source of compressed air through ensuring compatibility of the supply unit 100 with the source of compressed air.

The supply unit 100 may include an adjustable pressure regulator of the supply unit 100 that is used to adjust a fill pressure of the source of compressed air to ensure that the fill pressure does not exceed the design pressure of the air distribution system 150. Further, the supply unit may also include at least one pressure gauge of the supply unit enclosure to indicate any of the system pressure (e.g., the system pressure indicator 404) of the air distribution system and the fill pressure (e.g., the fill pressure indicator 400) of the source of compressed air.

FIG. 4B is a rear view of a supply unit 100, according to one embodiment. The supply unit also includes a series of valves 410 (e.g., a valve, an isolation valve, and/or a safety relief valve, etc.) to further ensure that system pressure is maintained within a safety threshold of the design pressure of the air distribution system.

The supply unit 100 of a building structure may facilitate delivery of breathable air from a source of compressed air to an air distribution system of the building structure. The supply unit 100 includes the series of valves 410 (e.g., the valve, and/or the safety relief valve, etc.) to prevent a leakage of the breathable air from the air distribution system potentially leading to loss of a system pressure. For example, the supply unit 100 may include the valve of the series of valves 410 to automatically suspend transfer of breathable air from the source of compressed air to the air distribution system when useful. The safety relief valve of the supply unit 100 and/or the fill site 102 may release breathable air when a system pressure of the air distribution system exceeds a threshold value beyond the design pressure to ensure reliability of the air distribution system through maintaining the system pressure such that it is within a pressure rating of each component of the air distribution system.

Figure 5:
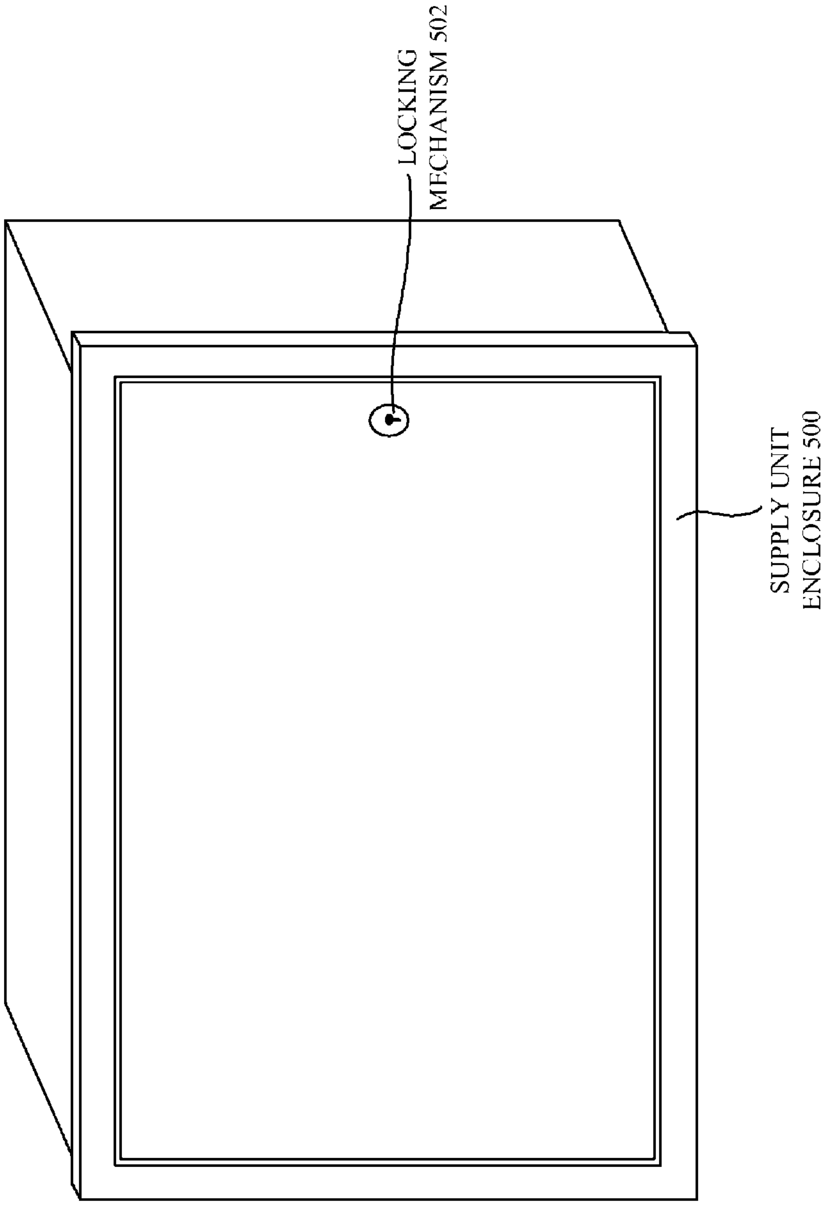
FIG. 5 is an illustration of a supply unit enclosure, according to one embodiment.

FIG. 5 is an illustration of a supply unit enclosure 500, according to one embodiment. The supply unit enclosure 500 may include a locking mechanism 502 to secure the supply unit 100 from unauthorized access. Further, the supply unit enclosure 500 may also contain fire rated material such that the supply unit 100 is able to withstand burning elevated temperatures.

Figure 6A:
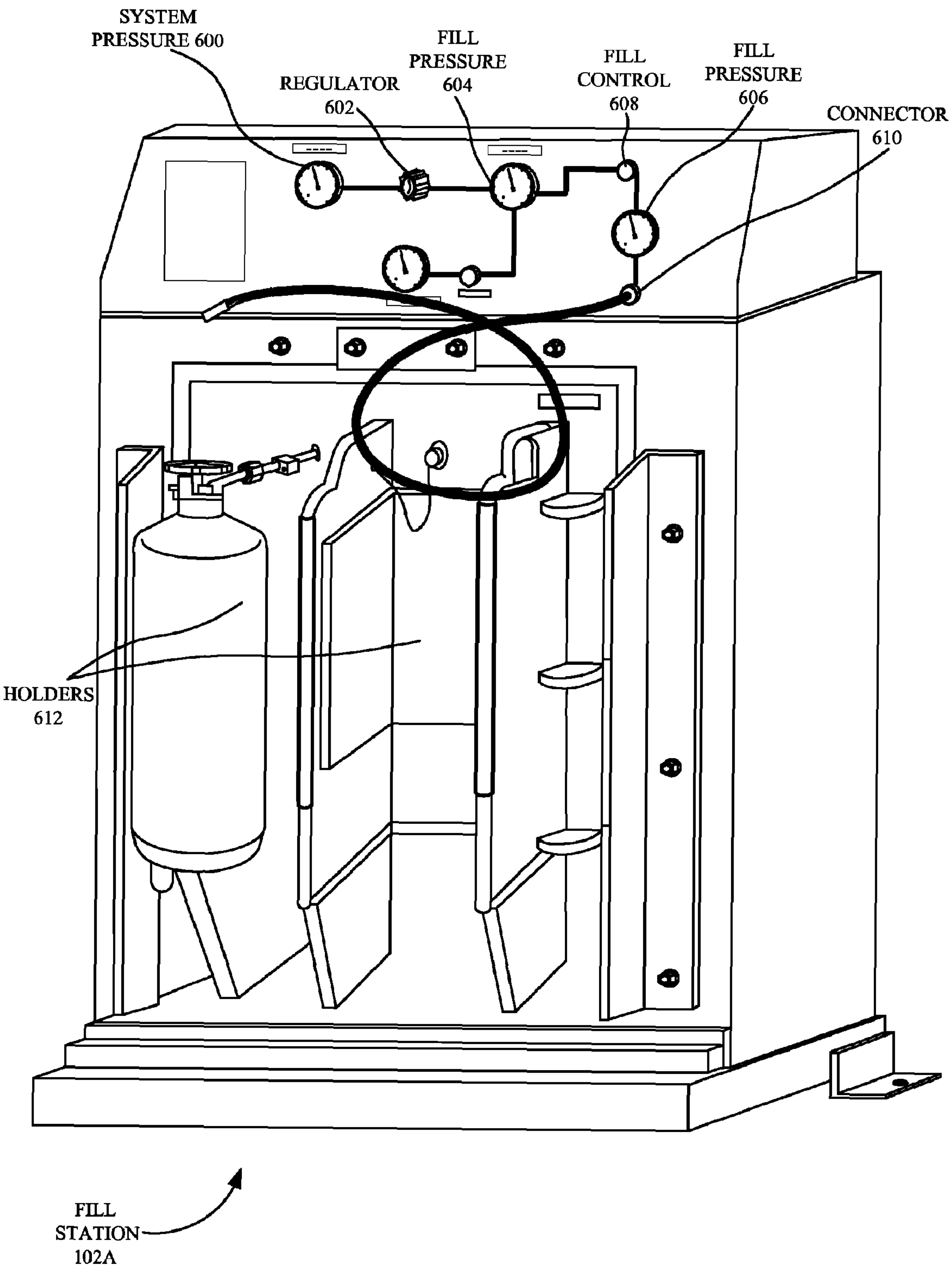
FIG. 6A is an illustration of a fill station, according to one embodiment.

The supply unit enclosure 500 encompassing the supply unit 100 may have any of a weather resistant feature, ultraviolet and infrared solar radiation resistant feature to prevent corrosion and physical damage. The locking mechanism 502 may secure the supply unit from intrusions that potentially compromise safety and reliability of the air distribution system. In addition, the supply unit enclosure 500 may include a robust metallic material of the supply unit enclosure 500 to minimize a physical damage due to various hazards to protect the supply unit 100 from any of an intrusion and damage. The robust metallic material may be at least substantially 18 gauge carbon steel. The supply unit enclosure 500 may include a visible marking to provide luminescence in a reduced light environment. The locking mechanism 502 may also include a tamper switch such that an alarm is automatically triggered and a signal is electrically coupled to any of a relevant administrative personnel of the building structure and the emergency supervising station when an intrusion of any of the supply unit and the secure chamber occurs. FIG. 6A is an illustration of a fill station 102A, according to one embodiment.

The fill station 102A may be a type of fill site (e.g., the fill site 102 as illustrated in FIG. 1). The fill station 102A may include a system pressure indicator 600, a regulator 602, a fill pressure indicator 604, another fill pressure indicator 606, and/or fill control knob 608. The fill station 102A may also include a connector 610 (e.g., a RIC (Rapid Interventions company)/UAC (Universal Air Connection) connector) and multiple breathable air apparatus holders 612 used to supply air from the air distribution system. The fill pressure indicator 604 may indicate the pressure level at which breathable air is being delivered by the source of compressed air to the air distribution system (e.g., an air distribution system 150, 250, and/or 350 of FIGS. 1-3). The system pressure indicator 600 may indicate the current pressure level of the breathable air in the air distribution system. The fill control knob 608 may be used to control the fill pressure such that the fill pressure does not exceed a safety threshold that the air distribution system is designed for. The connector 610 (e.g., RIC/UAC connector) may facilitate direct coupling to emergency equipment to supply breathable air through a hose that is connected to the connector 610 (e.g., RIC/UAC connector). In essence, precious time may be saved because the emergency personnel may not need to spend the time to remove the emergency equipment from their rescue attire before they can be supplied with breathable air. Further, the connector 610 (e.g., RIC/UAC connector) may also directly couple to a face-piece of a respirator to supply breathable air.

The multiple breathable air apparatus holders 612 can hold multiple compressed air cylinders to be filled simultaneously. In addition, the multiple breathable air apparatus holders 612 can be rotated such that additional compressed air cylinders may be loaded while the multiple compressed air cylinders are filled inside the fill station 102A. The fill station 102A may be a rupture containment chamber such that over pressurized compressed air cylinders are shielded and contained to prevent injuries.

In one embodiment, the fill station 102A interior to the building structure may provide the breathable air to a breathable air apparatus at multiple locations of the building structure. A secure chamber of the fill station 102A may be a safety shield that confines a possible rupture of an over-pressurized breathable air apparatus within the secure chamber. The fill station 102A may include a valve to prevent leakage of air from the air distribution system potentially leading to pressure loss of the air distribution system through ensuring that the system pressure is maintained within a threshold range of the design pressure to reliably fill the breathable air apparatus. An isolation valve may be included to isolate a breathable fill station from a remaining portion of the air distribution system.

The isolation valve may be automatically actuated based on an air pressure sensor of the air distribution system. The fill station 102A may include at least one pressure regulator to adjust a fill pressure to fill the breathable air apparatus and to ensure that the fill pressure does not exceed the pressure rating of the breathable air apparatus potentially resulting in a rupture of the breathable air apparatus. The fill station 102A may include a pressure gauge to indicate any of a fill pressure (e.g., the fill pressure indicator 604, and the fill pressure indicator 606) of the fill station and a system pressure (e.g., the system pressure indicator 600) of the air distribution system.

In one embodiment, the fill station 102A may have a physical capacity to enclose one or more breathable air apparatus and may include a RIC/UAC connector to facilitate a filling of the breathable air apparatus. Furthermore, the filling process of a breathable air apparatus may be safeguarded by enclosing the breathable air apparatus in a secure chamber and/or a secure device of a fill site of the emergency support system. The secure chamber may prevent the escape of the breathable air if the breathable air apparatus gets damaged during the filling process of the breathable air apparatus. Also, the breathable air apparatus may be secured to prevent the breathable air apparatus from injuring a user of the breathable air apparatus during the filling process of a breathable air apparatus.

The breathable air apparatus may be secured so as to ensure that the breathable air apparatus has access to air during the filling process. The fill station may also include a securing mechanism of the secure chamber of the fill station having a locking function, automatically actuated via a coupling mechanism with a flow switch that indicates a status of air flow to the breathable air apparatus that is fill able in the fill station.

Figure 6B:
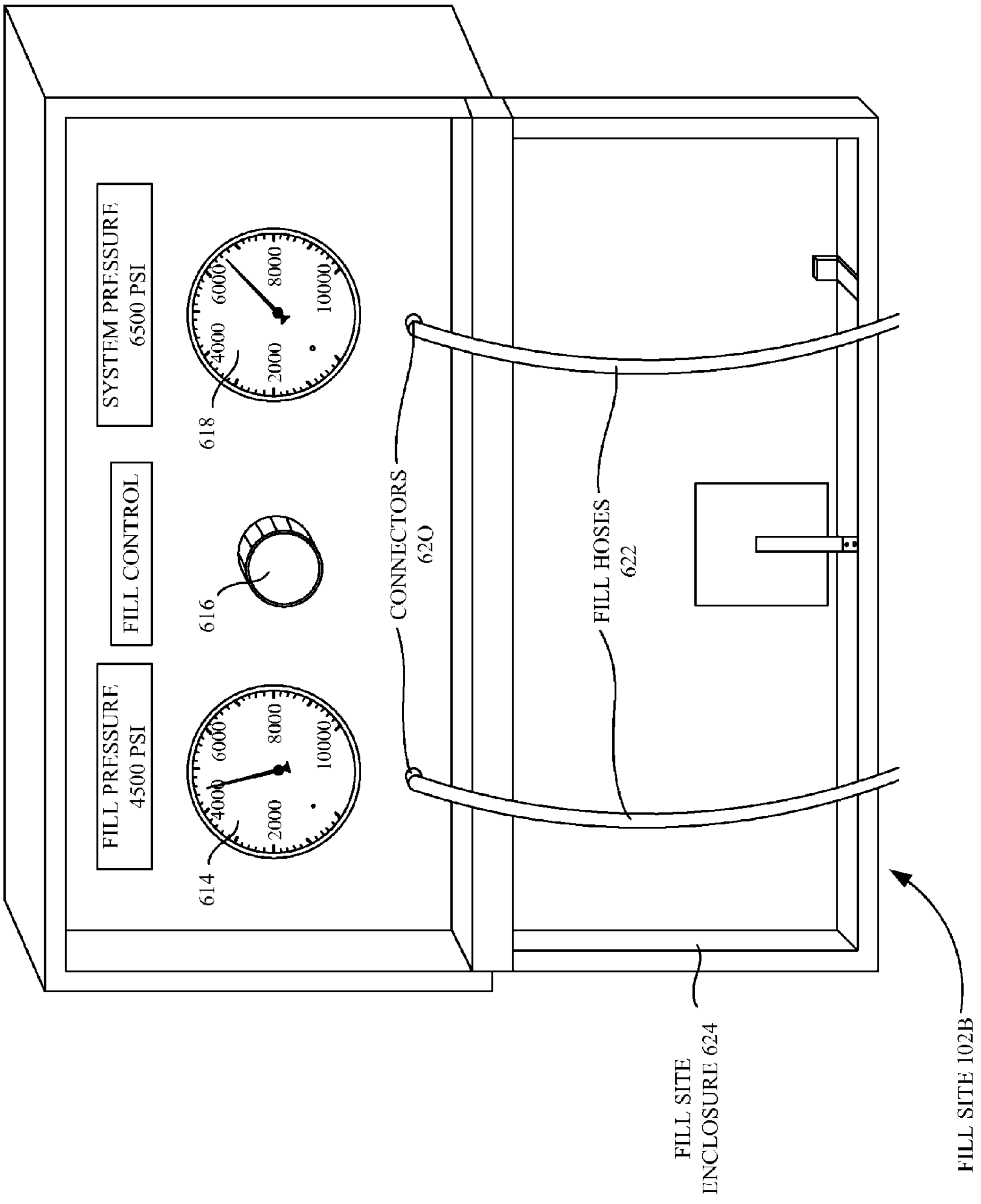
FIG. 6B is an illustration of a fill site, according to one embodiment.

FIG. 6B is an illustration of a fill panel (e.g., the fill site 102A), according to one embodiment. The fill site 102A (e.g., a fill panel) includes a fill pressure indicator 614 (e.g., pressure gauge), a fill control knob 616 (e.g., pressure regulator), a system pressure indicator 618, a number of connectors 620 (e.g., RIC/UAC connector), and/or fill hoses 622. The fill site 102A may also include a locking mechanism of a fill site enclosure 624 (e.g., fill panel enclosure) to secure the fill site 102A from intrusions that potentially compromise safety and reliability of the air distribution system. The system pressure indicator 618 may indicate the current pressure level of the breathable air in the air distribution system. The fill control knob 616 (e.g., pressure regulator) may be used to adjust the fill pressure such that the fill pressure does not exceed a safety threshold that the air distribution system is designed for. In one or more embodiments, it should be noted that the connector described herein is a RIC/UAC connector.

The RIC/UAC connector 620 may facilitate direct coupling to emergency equipment to supply breathable air through a hose that is connected to the RIC/UAC connector 620. In essence, precious time may be saved because the emergency personnel may not need to spend the time to remove the emergency equipment from their rescue attire before they can be supplied with breathable air. Further, the RIC/UAC connector 620 connected with the fill hoses 622 may also directly couple to a face-piece of a respirator to supply breathable air to either emergency personnel (e.g., a fire fighter, a SWAT team, a law enforcer, and/or a medical worker, etc.) and/or stranded survivors in need of breathing assistance. Each of the fill hoses 622 may have different pressure rating of the fill site 102A is couple-able to any of a self-contained breathable air apparatus and respiratory mask having a compatible connector (e.g., RIC/UAC connector). The fill site enclosure 624 may include a visible marking to provide luminescence in a reduced light environment.

The fill site 102A interior to the building structure may have the connector (e.g., the RIC/UAC connector 620) to fill a breathable air apparatus to expedite a breathable air extraction process from the air distribution system and to provide the breathable air to the breathable air apparatus at multiple locations of the building structure. The fill site 102A may include a safety relief valve set to have an open pressure of at most approximately 10% more than a design pressure of the air distribution system to ensure reliability of the air distribution system through maintaining the system pressure such that it is within a threshold range of a pressure rating of each component of the air distribution system. The fill site enclosure 624 may comprise of at least 18 gauge carbon steel to minimize physical damage of various naturally occurring and man-imposed hazards through protecting the fill site from any of an intrusion and damage. The fill site 102A may include an isolation valve to isolate a damaged fill site from a remaining operable portion of the air distribution system.

In an alternate embodiment, a fill station may be a type of fill site 102 of FIG. 1. The fill station may include a system pressure indicator, a regulator, a fill pressure indicator, another fill pressure indicator, and/or fill control knob. The fill station may also include a connector (e.g., a RIC/UAC connector) and multiple breathable air apparatus holders used to supply air from the air distribution system (e.g., the air distribution system 150, 250, and/or 350 of FIGS. 1-3). The fill pressure indicator may indicate the pressure level at which breathable air is being delivered by the source of compressed air to the air distribution system (e.g., the air distribution system 150, 250, and/or 350 of FIGS. 1-3). The system pressure indicator may indicate the current pressure level of the breathable air in the air distribution system. The fill control knob may be used to control the fill pressure such that the fill pressure does not exceed a safety threshold that the air distribution system is designed for. The RIC/UAC connector 620 may facilitate direct coupling to emergency equipment to supply breathable air through a hose (e.g., fill hoses 622) that is connected to the connector RIC/UAC 620. In essence, precious time may be saved because the emergency personnel may not need to spend the time to remove the emergency equipment from their rescue attire before they can be supplied with breathable air. Further, the RIC/UAC connector 620 may also directly couple to a face-piece of a respirator to supply breathable air.

The multiple breathable air apparatus holders can hold multiple compressed air cylinders to be filled simultaneously. In addition, the multiple breathable air apparatus holders can be rotated such that additional compressed air cylinders may be loaded while the multiple compressed air cylinders are filled inside the fill station. The fill station may be a rupture containment chamber such that over-pressurized compressed air cylinders are shielded and contained to prevent injuries.

In one embodiment, the fill station interior to the building structure may provide the breathable air to a breathable air apparatus at multiple locations of the building structure. A secure chamber of the fill station may be a safety shield that confines a possible rupture of an over-pressurized breathable air apparatus within the secure chamber. The fill station may include a valve to prevent leakage of air from the air distribution system potentially leading to pressure loss of the air distribution system through ensuring that the system pressure is maintained within a threshold range of the design pressure to reliably fill the breathable air apparatus. An isolation valve may be included to isolate a breathable fill station from a remaining portion of the air distribution system.

The isolation valve may be automatically actuated based on an air pressure sensor of the air distribution system. The fill station may include at least one pressure regulator to adjust a fill pressure to fill the breathable air apparatus and to ensure that the fill pressure does not exceed the pressure rating of the breathable air apparatus potentially resulting in a rupture of the breathable air apparatus. The fill station may include one or more pressure gauge to indicate any of a fill pressure (e.g., the fill pressure indicator) of the fill station and a system pressure (e.g., the system pressure indicator) of the air distribution system. In one embodiment, the fill station may have a physical capacity to enclose one or more breathable air apparatuses and may include the connector 620 (e.g., a RIC/UAC connector) to facilitate a filling of the breathable air apparatus. The fill station may also include a securing mechanism of the secure chamber of the fill station having a locking function is automatically actuated via a coupling mechanism with a flow switch that indicates a status of air flow to the breathable air apparatus that is tillable in the fill station. The fill panel described herein may also protect the RIC/UAC fittings from fire or physical damage by providing an enclosure and sufficient padding (e.g., fire rated material) within the enclosure.

Figure 7B:
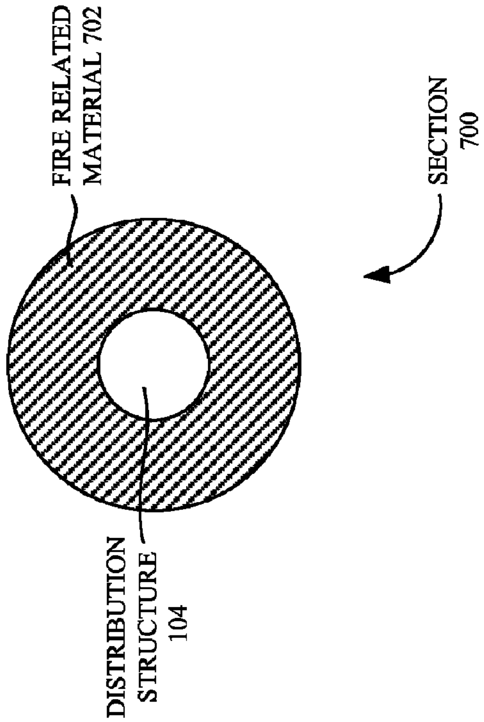
FIG. 7B is a cross sectional view of a piping structure embedded in a fire rated material, according to one embodiment.
Figure 7A:
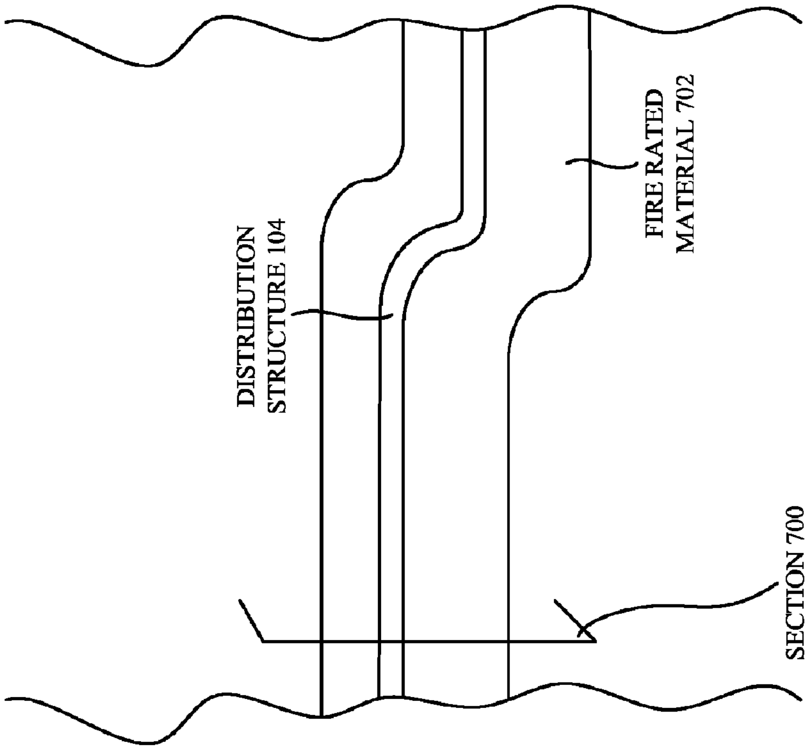
FIG. 7A is a diagrammatic view of the distribution structure embedded in a fire rated material, according to one embodiment.

FIG. 7A is a diagrammatic view of a distribution structure 104 embedded in a fire rated material, according to one embodiment. The distribution structure 104 (e.g., a piping structure) may be enclosed in the fire rated material 702. The fire rated material may prevent the distribution structure 104 from damage in a fire such that an air distribution system (e.g., the air distribution system 150, 250, 350 of FIGS. 1-3) may be operational for a longer time period in an emergency situation (e.g., a building fire, a chemical attack, terror attack, subway accident, mine collapse, and/or a biological agent attack, etc.). Section 700 is a cross section of the distribution structure 104 embedded in the fire rated material 702.

FIG. 7B is a cross sectional view 700 of a piping structure embedded in a fire rated material, according to one embodiment. Section 700 is a cross section of the distribution structure 104 embedded in the fire rated material 702.

Figure 8:
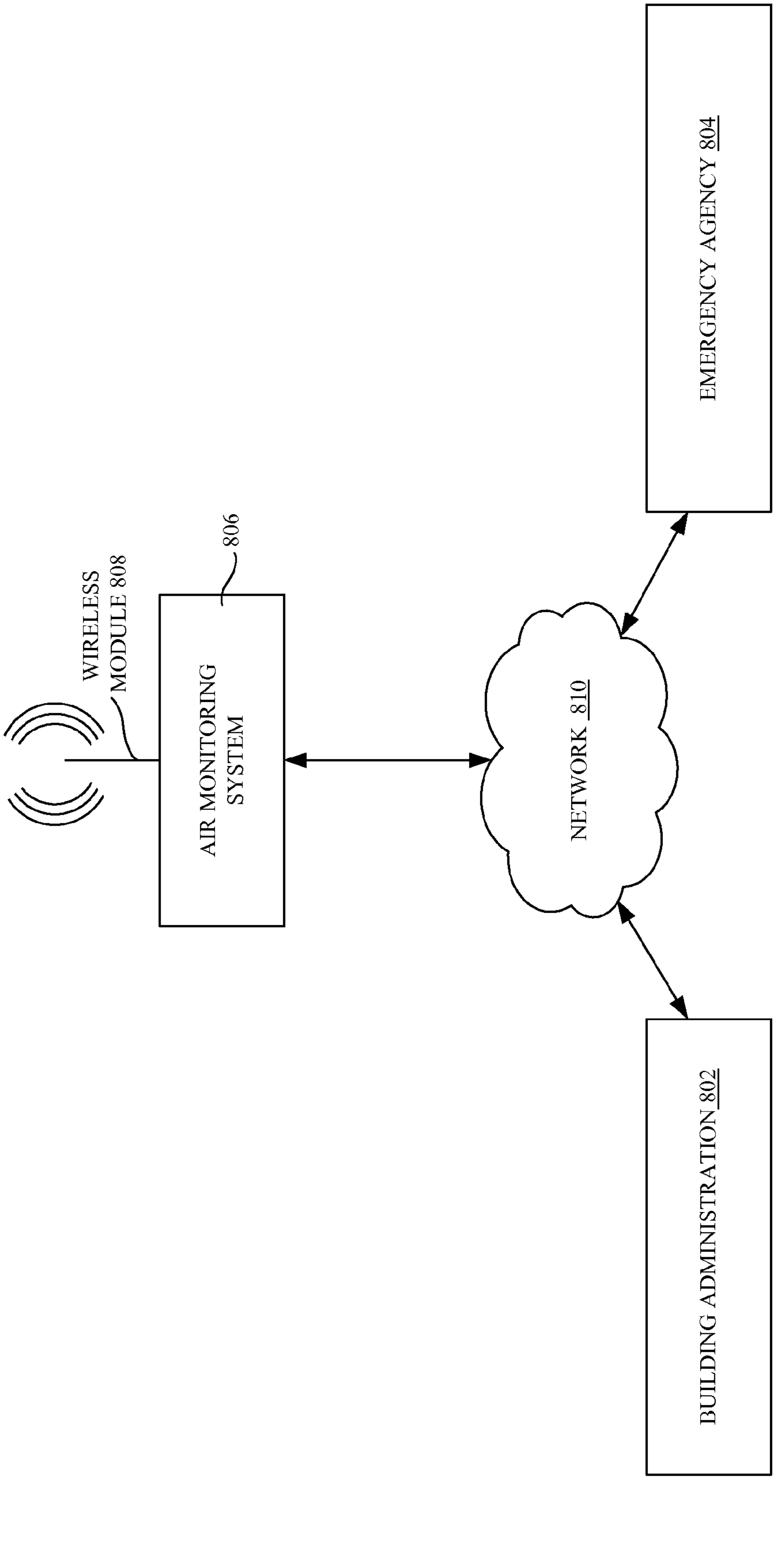
FIG. 8 is a network view of an air monitoring system communicating to a building administration and an authority agency, according to one embodiment.

FIG. 8 is a network view of an air monitoring system 806 with a wireless module 808 that communicates with a building administration 802 and an authority agency 804 through a network 810, according to one embodiment.

The air monitoring system 806 may include various sensors (e.g., CO/moisture sensor 106 of FIG. 1, pressure sensor 108 of FIG. 1, and/or hazardous substance sensor, etc.) and/or status indicators regarding system readiness information (e.g., system pressure, in use, not in use, operational status, fill site usage status, fill site operational status, etc.). The air monitoring system 806 may communicate sensor readings to a building administration 802 (e.g., building management, security, and/or custodial services, etc.) such that proper maintenance measures may be taken. The air monitoring system 806 may also send alerting signals as a reminder for regular system inspection and maintenance to the building administration 802 through the network 810. The air monitoring system 806 may also communicate sensor readings to an authority agency 804 (e.g., a police station, a fire station, and/or a hospital, etc.).

Figure 9:
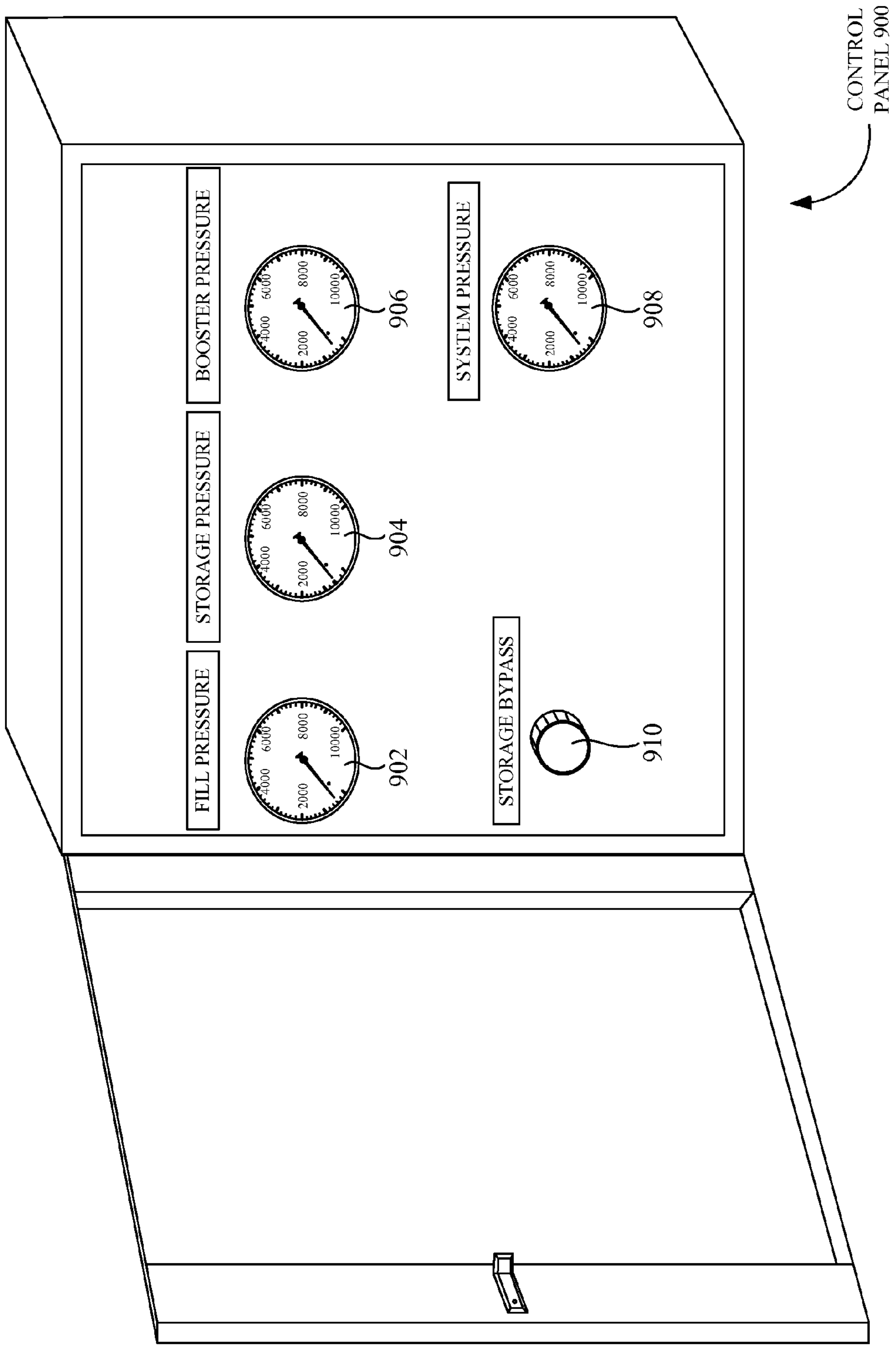
FIG. 9 is a front view of a control panel of an air storage sub-system, according to one embodiment.

FIG. 9 is a front view of a control panel 900 of an air storage sub-system, according to one embodiment. The control panel 900 includes a fill pressure indicator 902, a storage pressure indicator 904, a booster pressure indicator 906, a system pressure indicator 908 and/or a storage bypass 910. The fill pressure indicator 902 may indicate the pressure level at which breathable air is being delivered by the source of compressed air to the air distribution system (e.g., an air distribution system 150, 250, and/or 350 of FIGS. 1-3). The storage pressure indicator 904 may display the pressure level of air storage tanks in the air storage sub-system. The booster pressure indicator may display the pressure level of a booster cylinder. The system pressure indicator 908 may indicate the current pressure level of the breathable air in the air distribution system. Breathable air may be directly supplied to the air distribution system (e.g., an air distribution system 150, 250, and/or 350 of FIGS. 1-3) through the storage bypass 910.

Figure 10:
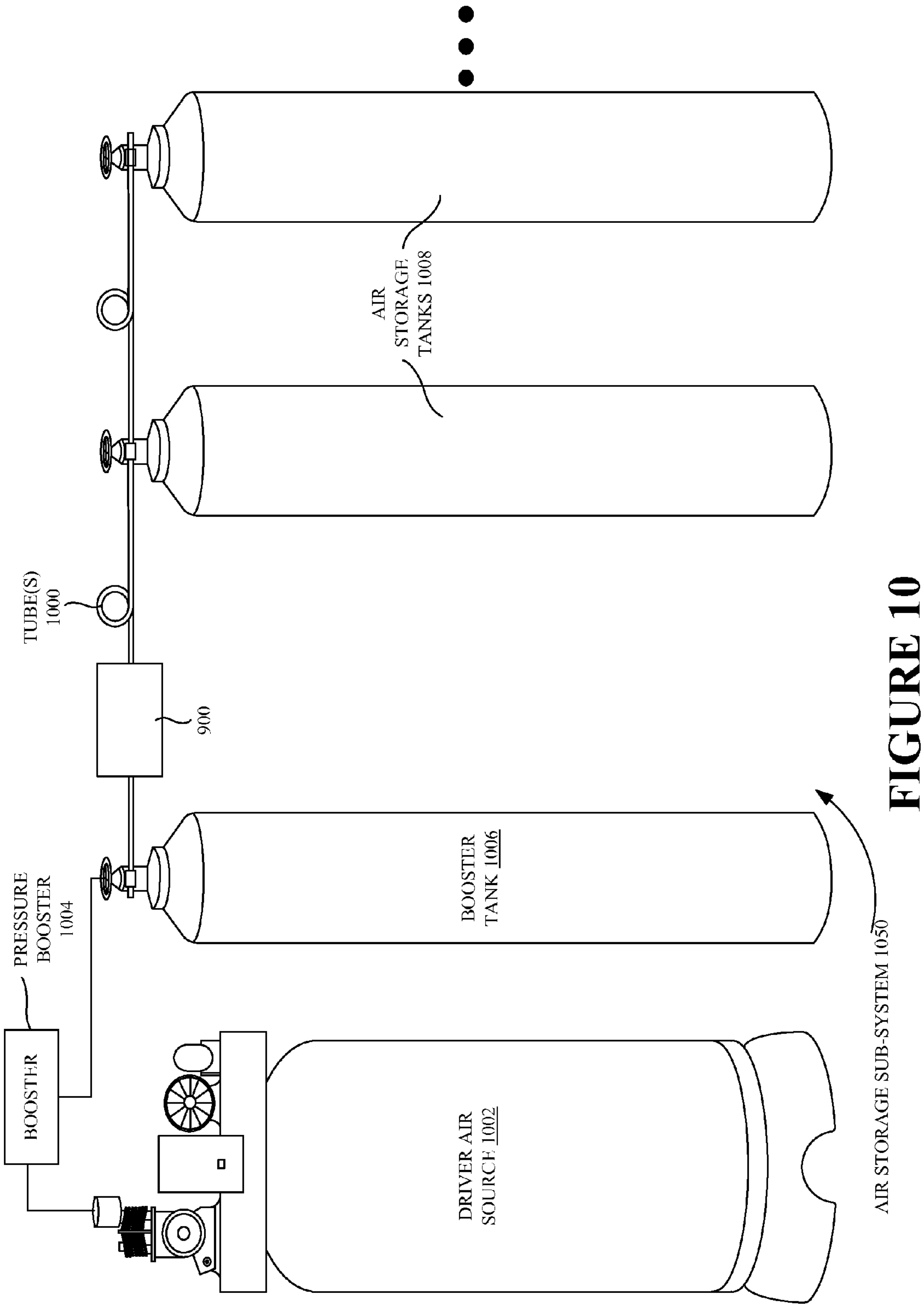
FIG. 10 is an illustration of an air storage sub-system, according to one embodiment.

FIG. 10 is an illustration of an air storage sub-system 1050, according to one embodiment. The air storage sub-system 1050 may include a control panel 900, tubes 1000, a driver air source 1002, a pressure booster 1004, a booster tank 1006, and/or any number of air storage tanks 1008. The control panel 900 may provide status information regarding the various components of the air storage sub-system 1050. The tubes 1000 may couple each of the air storage tanks 1008 to one another in a looped configuration to increase robustness of the tubes 1000. The driver air source 1002 may be used to pneumatically drive the pressure booster 1004 to maintain a higher pressure of the air distribution system such that a breathable air apparatus is reliably filled. The booster tank 1006 may store air at a higher pressure than the air stored in the air storage tanks 1008 to ensure that the air distribution system can be supplied with air that is sufficiently pressurized to fill a breathable air apparatus.

In one embodiment, the air storage sub-system 1050 may include air storage tanks 1008 to provide a storage of air that is dispersible to multiple locations of the building structure. The number of air storage tanks 1008 of the air storage sub-system 1050 may be coupled to each other through tubes 1000 having a looped configuration to increase robustness of the tubes 1000 through preventing breakage due to stress. In addition, a booster tank (e.g., the booster tank 1006) of the air storage sub-system 1050 may be coupled to the plurality of air storage tanks to store compressed air of a higher pressure than the compressed air that is stored in the air storage tanks 1008. A driver air source 1002 of the air storage sub-system 1050 may be coupled to a pressure booster (e.g., the pressure booster 1004) to pneumatically drive a piston of the pressure booster (e.g., the pressure booster 1004) to maintain a higher pressure of the air distribution system such that a breathable air apparatus is reliably filled.

Further, the driver air source may enable the breathable air to be optimally supplied to the building structure through allowing the breathable air to be isolated from driving the pressure booster 1004. The air storage sub-system 1050 may also include an air monitoring system (e.g., the carbon monoxide sensor and moisture sensor 106 of FIGS. 1-3) to automatically track and record any of impurities and contaminants in the breathable air of the air distribution system. The air monitoring system 110 of FIGS. 1-3 may include an automatic shut down feature to suspend air dissemination to the fill stations (e.g., the fill station) in a case that any of impurity levels and contaminant levels exceed a safety threshold. The air storage sub-system 1050 may also include a pressure monitoring system (e.g., a pressure sensor 108 of FIG. 1) to continuously track and record the system pressure of the air distribution system (e.g., the air distribution system 150, 250, 350 of FIGS. 1-3). In addition, a pressure switch may be electrically coupled to an alarm system such that the alarm system is set off when the system pressure of the air distribution system (e.g., the air distribution system 150, 250, 350 of FIGS. 1-3) is outside a safety range. The pressure switch (e.g., a pressure sensor 108 of FIG. 1) may electrically transmit a warning signal to an emergency supervising station when the system pressure of the air distribution system (e.g., the air distribution system 150, 250, 350 of FIGS. 1-3) is below the prescribed level.

The air storage sub-system 1050 may include at least one indicator unit to provide status information of the air distribution system (e.g., the air distribution system 150, 250, 350 of FIGS. 1-3) including storage pressure, booster pressure, pressure of the compressed air source, and the system pressure. Further, the air storage sub-system 1050 may also include a selector valve that is accessible by an emergency personnel to isolate the source of compressed air from the air storage sub-system such that the breathable air of the source of compressed air is directly deliverable to the fill site (e.g., the fill site 102A of FIG. 6) through the distribution structure. The air storage sub-system 1050 may be housed in a fire rated enclosure that is certified to be rupture containable to withstand elevated temperatures for a period of time.

Figure 11:
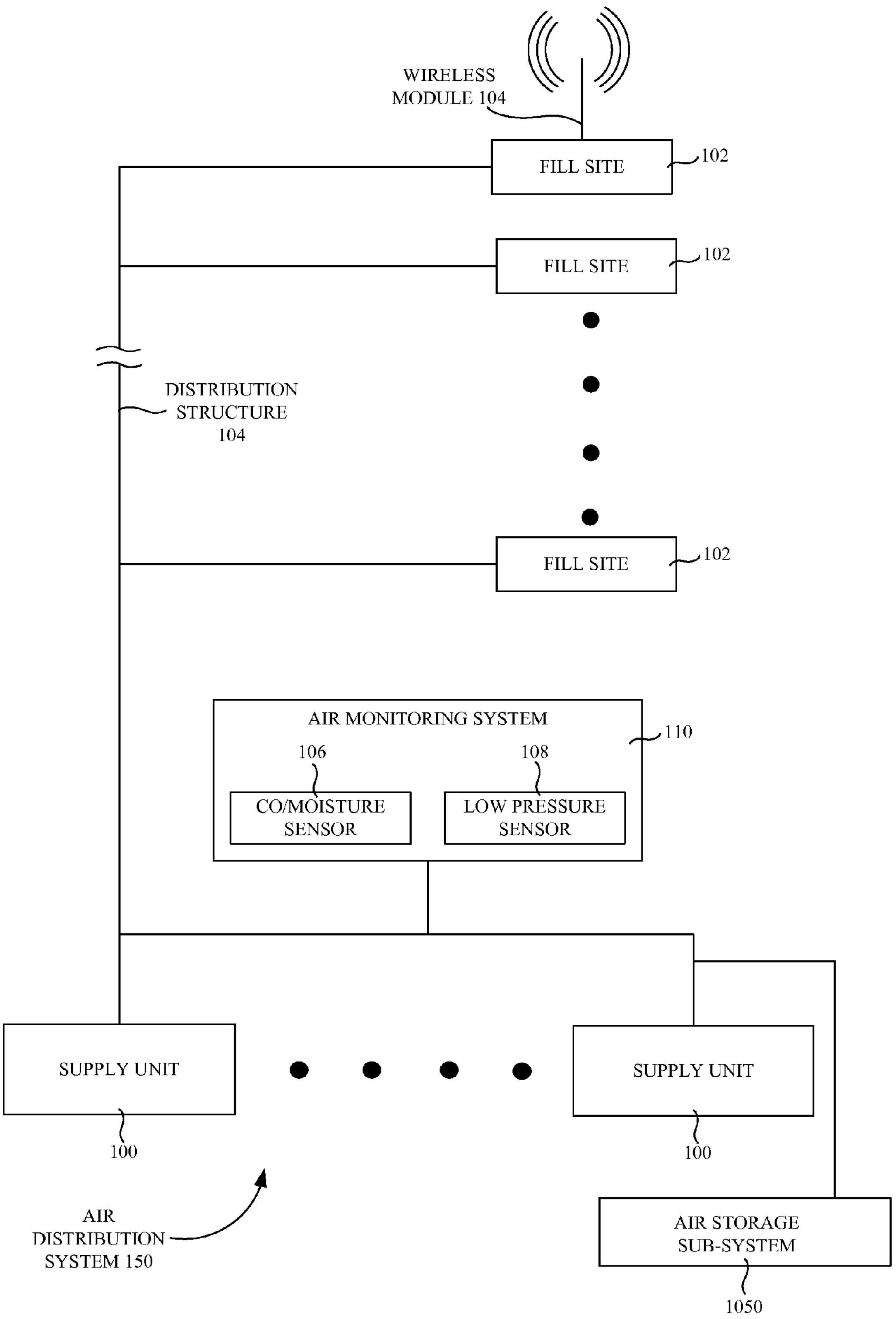
FIG. 11 is a diagram of the air distribution system having an air storage sub-system, according to one embodiment.

FIG. 11 is a diagram of the air distribution system 150 having an air storage sub-system 1050, according to one embodiment. The air distribution system 150 may include any number of the supply unit 100, any number of fill sites (e.g., the fill site 102A of FIG. 6) that are coupled to the rest of the air distribution system 150 through a distribution structure 104. The air distribution system 150 may also include an air monitoring system 110 having a CO/Moisture sensor 106 and a pressure sensor 108, and/or the air storage sub-system 1050. The air storage sub-system 1050 is as previously described. Air storage tanks 1008 and/or a booster tank 1006 of the air storage sub-system 1050 of FIG. 10 may be supplied with breathable air through a source of compressed air that is coupled to the air distribution system through the supply unit 100 and/or supplied independently of the supply unit 100. The air storage sub-system 1050 may provide a spare source of breathable air to the air distribution system (e.g., the air distribution system 150, 250, 350 of FIGS. 1-3) in addition to an external source of compressed air.

Figure 12:
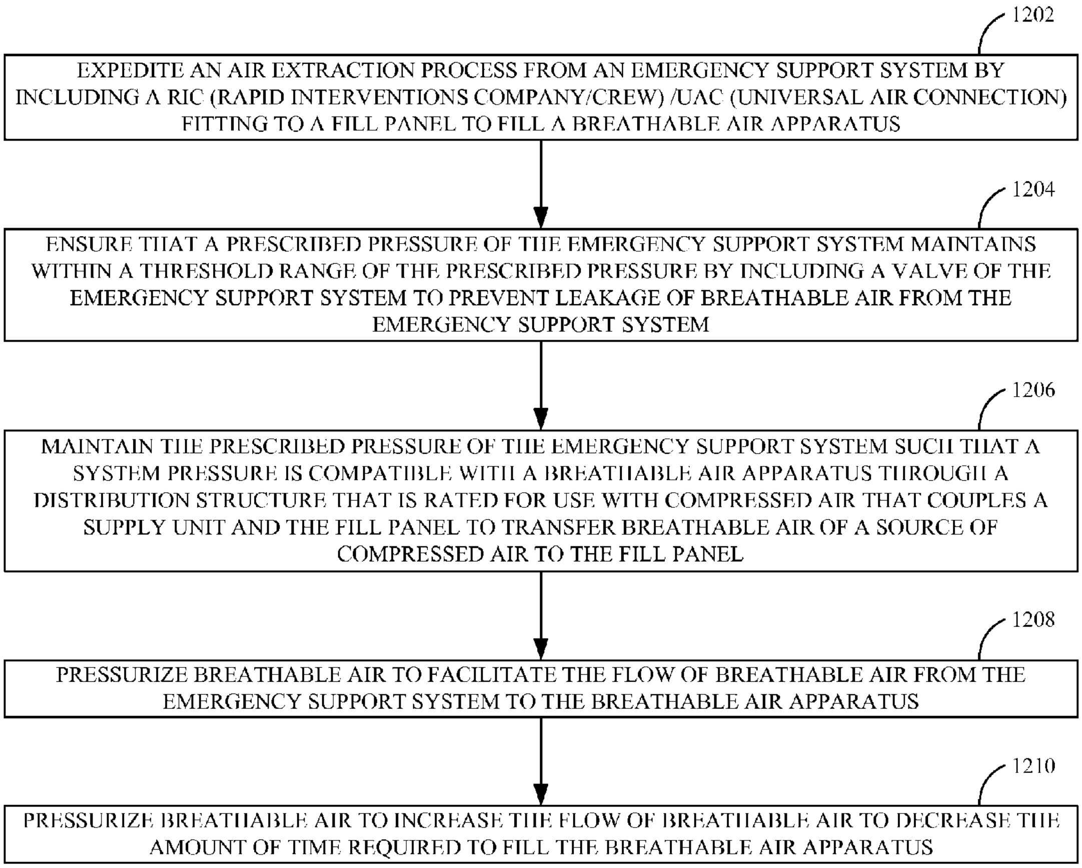
FIG. 12 is a process flow of maintaining safety of a mine structure, according to one embodiment.

FIG. 12 is a process flow of maintaining safety of a mine structure, according to one embodiment. In operation 1202, an air extraction process from an emergency support system may be expedited by including the RIC/UAC fitting to the fill panel (e.g., the fill site 102A-N) to fill the breathable air apparatus. In operation 1204, a prescribed pressure of the emergency support system being maintained within a threshold range of the prescribed pressure may be ensured by including a valve of the emergency support system to prevent leakage of breathable air from the emergency support system. In operation 1206, the prescribed pressure of the emergency support system may be maintained such that a system pressure is compatible with a breathable air apparatus through a distribution structure that is rated for use with compressed air that couples the supply unit 100 and the fill panel to transfer breathable air of a source of compressed air to the fill panel.

The prescribed pressure of the emergency support system may be designated based on a pressure rating (e.g., provided by the Standard on Open-Circuit Breathing Apparatus for emergency services) of the breathable air apparatus. The prescribed pressure of the emergency support system may be designated based on a regulation (e.g., the regulation provided by the National Fire Protection Association and Standard on Open-Circuit Breathing Apparatus) that specifies a pressure rating of the breathable air apparatus. In operation 1208, the breathable air may be pressurized to facilitate a flow of breathable air from the emergency support system to the breathable air apparatus. In operation 1210, the breathable air may be pressurized to increase the flow of breathable air to decrease an amount of time required to fill the breathable air apparatus.

Figure 13:
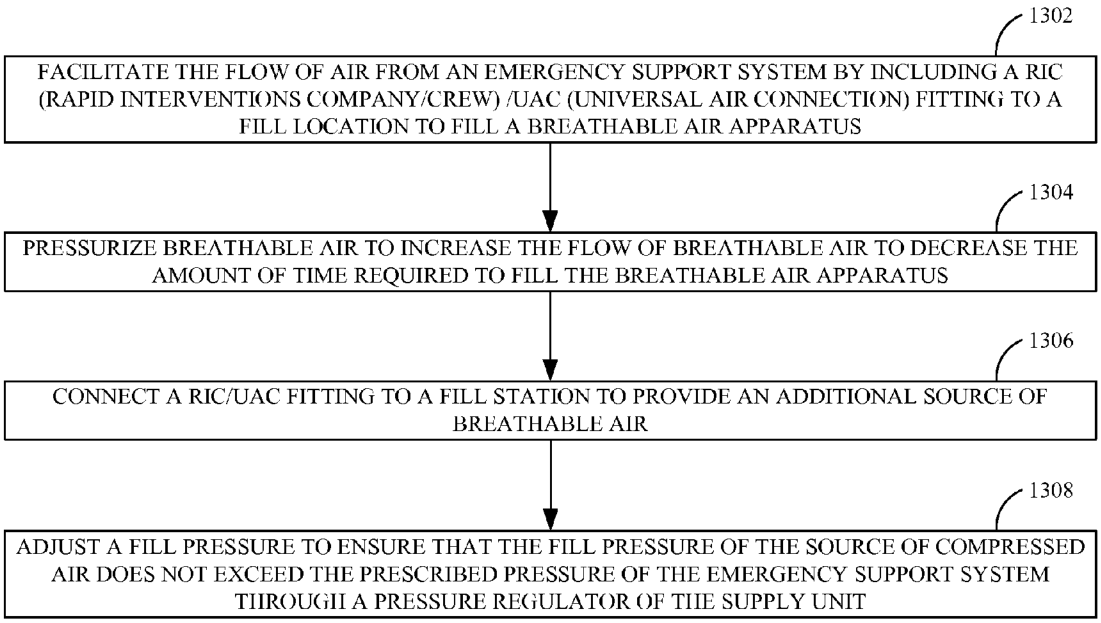
FIG. 13 is a process flow of managing a flow of air in an emergency support system, according to one or more embodiments.

FIG. 13 is a process flow of managing a flow of air in an emergency support system, according to one or more embodiments. In operation 1302, a flow of air from an emergency support system may be facilitated by including the RIC/UAC fitting to a fill location to fill a breathable air apparatus. In operation 1304, breathable air may be pressurized to increase the flow of breathable air to decrease an amount of time required to fill the breathable air apparatus. In operation 1306, the RIC/UAC fitting may be connected to a fill station to provide an additional source of breathable air. In operation 1308, a fill pressure may be adjusted to ensure that the fill pressure of the source of compressed air does not exceed the prescribed pressure of the emergency support system through a pressure regulator of the supply unit.

Figure 14:
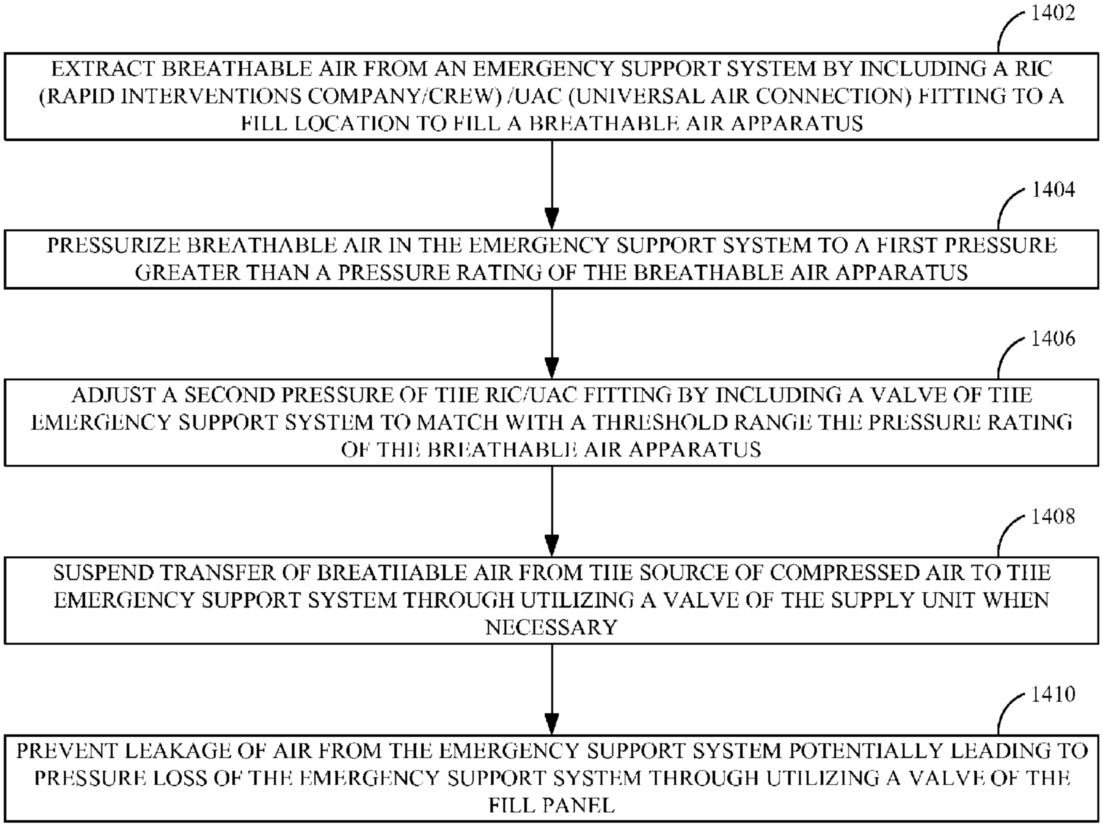
FIG. 14 is a process flow of maintaining pressure in the system, according to one embodiment.

FIG. 14 is a process flow of maintaining pressure in the system, according to one embodiment. In operation 1402, breathable air may be extracted from an emergency support system by including the RIC/UAC fitting to a fill location to fill a breathable air apparatus. In operation 1404, the breathable air in the emergency support system may be pressurized to a first pressure greater than a pressure rating of the breathable air apparatus. In operation 1406, a second pressure of the RIC/UAC fitting may be adjusted by including a valve of the emergency support system to match with a threshold range the pressure rating of the breathable air apparatus. In operation 1408, transfer of breathable air from the source of compressed air to the emergency support system may be suspended through utilizing a valve of the supply unit when necessary. In operation 1410, leakage of air from the emergency support system potentially leading to pressure loss of the emergency support system may be prevented through utilizing a valve of the fill panel. The fill panel may protect the RIC/UAC fitting from fire and physical damage.

Figure 15:
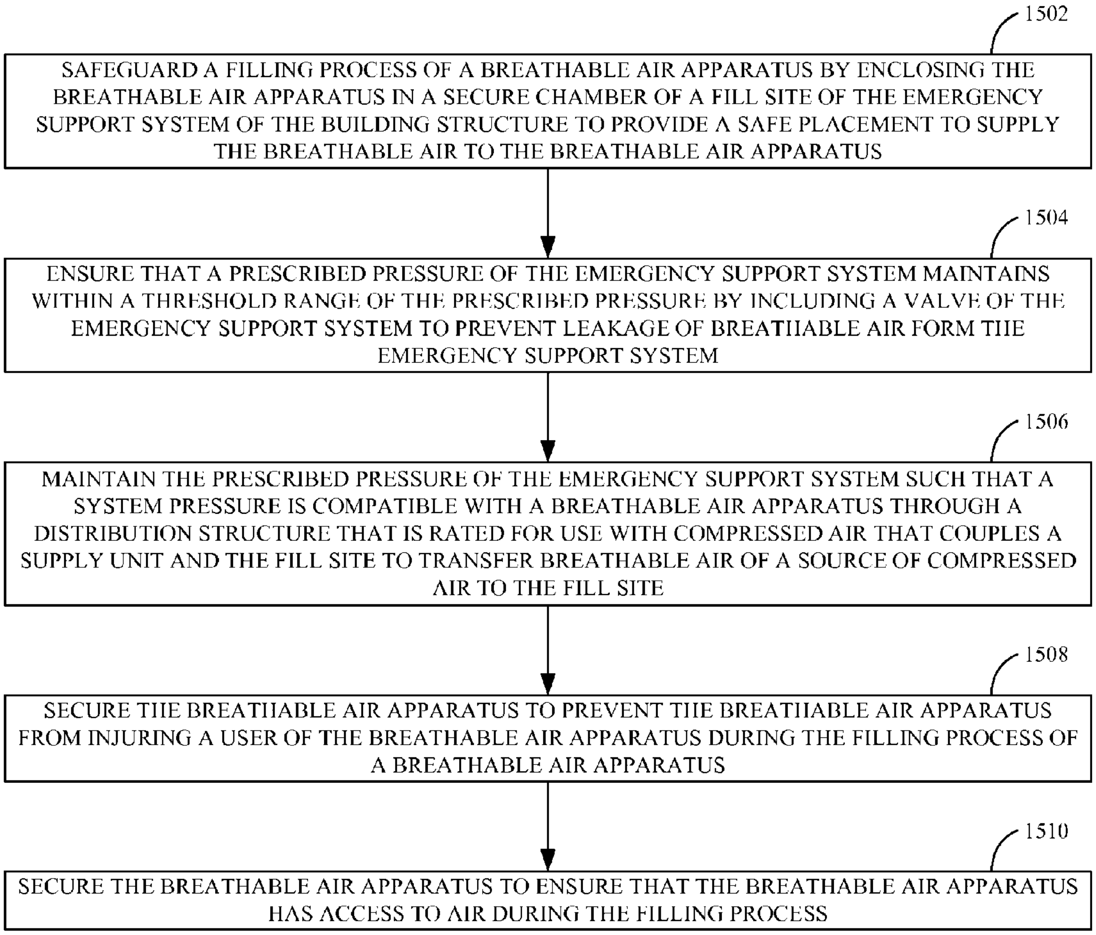
FIG. 15 is a process flow illustrating a method of safeguarding a filling process of a breathable air apparatus, according to one embodiment

FIG. 15 is a process flow illustrating a method of safeguarding a filling process of a breathable air apparatus, according to one embodiment. In operation 1502, a filling process of a breathable air apparatus may be safeguarded by enclosing the breathable air apparatus in a secure chamber of a fill site (e.g., the fill site 102 of FIG. 1) of the emergency support system of the building structure. The filling process of the breathable air apparatus may be safeguarded to provide a safe placement to supply the breathable air to the breathable air apparatus.

In operation 1504, a prescribed pressure of the emergency support system may be ensured to be within a threshold range of the prescribed pressure by including a valve of the emergency support system to prevent leakage of breathable air from the emergency support system. In operation 1506, the prescribed pressure of the emergency support system may be maintained such that a system pressure is compatible with a breathable air apparatus through the distribution structure 104 that is rated for use with the compressed air. In operation 1508, the breathable air apparatus may be secured to prevent the breathable air apparatus from injuring a user of the breathable air apparatus during the filling process of a breathable air apparatus. In operation 1510, the breathable air apparatus may be secured to ensure that the breathable air apparatus has access to air during the filling process.

Figure 16:
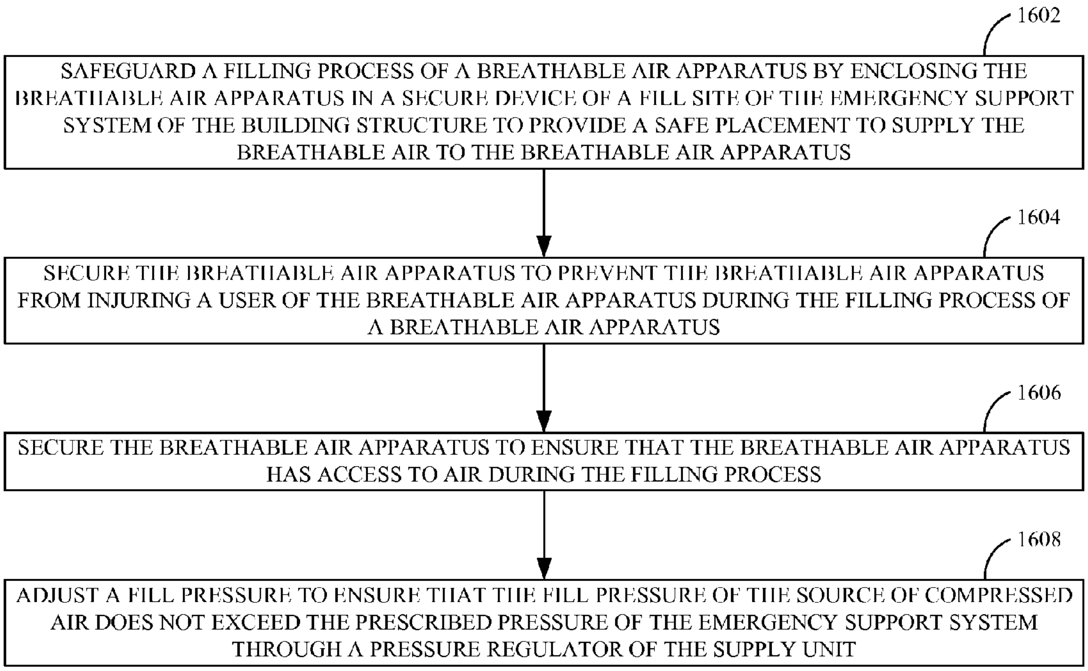
FIG. 16 is a process flow illustrating a method of safeguarding a filling process of a breathable air apparatus, according to another embodiment.

FIG. 16 is a process flow illustrating a method of safeguarding a filling process of a breathable air apparatus, according to another embodiment. In operation 1602, a filling process of a breathable air apparatus may be safeguarded by enclosing the breathable air apparatus in a secure device of the fill site 102 of the emergency support system of the building structure to provide a safe placement to supply the breathable air to the breathable air apparatus. The secure device may prevent the escape of the breathable air in case the breathable air apparatus is damaged during the filling process of the breathable air apparatus. In operation 1604, the breathable air apparatus may be secured to prevent the breathable air apparatus from injuring a user of the breathable air apparatus during the filling process of a breathable air apparatus. In operation 1606, the breathable air apparatus may be secured to ensure that the breathable air apparatus has access to air during the filling process. In operation 1608, a fill pressure may be adjusted to ensure that the fill pressure of the source of compressed air does not exceed the prescribed pressure of the emergency support system through a pressure regulator of the supply unit.

In an embodiment, a safety system of a structure may include the fill (e.g., supply, put, add, spread throughout, make full, etc.) station (e.g., a location along a route, an apparatus with special equipment, a place to load and/or unload, etc.) in the underground mine. The fill station (e.g., the fill site 102A-N) may include a mechanism to add breathable air to an air tank of a Self Contained Breathing Apparatus (SCBA) unit within a secure (e.g., free from danger and/or injury, dependable, unlikely to fail, etc.) chamber (e.g., a compartment, an enclosed space, a cavity, etc.) of the underground mine. The secure chamber (e.g., supply unit enclosure 500) may act as a safety shield (e.g., a protective barrier to prevent injury and/or avert danger, a structure to prevent escape, etc.) that confines (e.g., to close within bounds, prevent from leaving, limit, etc.) a possible rupture (e.g., explosion, fragmentation, disintegration, etc.) of an over-pressurized breathable air apparatus (e.g., a SCBA air tank, etc.) within the secure chamber.

The fill station may therefore prevent injury or death from an exploding air cylinder by using a structure that substantially encloses the air cylinder on all sides, that restricts a fill operation to when the enclosure is closed and locked, and/or that substantially prevents air tank fragments above a threshold size from emerging from the enclosure. The fill station may also include a structure that is capable of withstanding shrapnel, that uses a locking mechanism (e.g., the locking mechanism 502) to enclose the air tank within the structure, and/or that includes a cylinder rotational mechanism allows simultaneous connection and disconnection of air cylinders while cylinders are being filled internally. The walls of the secure chamber (e.g., supply unit enclosure 500) may be made of a continuous material, welded, bolted, and/or attached in any other means required to sustain forces associated with an explosive venting of compressed gas. The secure chamber (e.g., supply unit enclosure 500) of the fill station may also be required to meet a certification standard.

An open-circuit rescue or firefighter SCBA may include various components, including a full-face mask, regulator, air cylinder, cylinder pressure gauge, and a harness with adjustable shoulder straps and waist belt that allows it be worn on a user's back. Air cylinders for SCBA may be made of aluminum, steel, and/or a composite construction (e.g., carbon-fiber wrapped). The composite cylinders may be the lightest in weight, which may make them preferred by fire departments. However, they may also have the shortest lifespan out of various types of air cylinders, and they may be taken out of service after 15 years. The air cylinder may come in one of three standard sizes: 30, 45 or 60 minutes of breathing time. Cylinders may be filled to a standard pressure rating (e.g., 3000 psi, 4500 psi, etc.) of several thousand pounds per square inch. While many cylinders may be used repeatedly and safely with proper maintenance and inspection, some air cylinders have explosively ruptured in the past, causing injury and/or death.

Required testing may include a visual inspection in which a tank's interior is checked for corrosion, particulate, and/or any other abnormalities. The threads may be checked for integrity and/or imperfections. On aluminum tanks, a special electronic device may be used to check a cylinder's neck threads for cracking (e.g., stress cracks). An annual or more frequent inspection by an experienced technician may be needed to detect hazardous cracking before the cylinder becomes likely to fail. Untrained technicians may be unable to identify features associated with air cylinder inspections (e.g., a valley, a fold, a tap stop, etc.). Untrained technicians may also be unaware of how many threads may be safely penetrated before a cylinder must be discarded.

Air cylinders may further be required to undergo regular hydrostatic testing (e.g., every 3 years for composite cylinders, every 5 years for metal cylinders). A hydrostatic test is the common way in which leaks and/or flaws can be found in pressure vessels such as a gas cylinder. During hydrostatic testing, an air cylinder may be filled with a nearly incompressible liquid (e.g., water, oil, etc.) and examined for leaks or permanent changes in shape. Red or fluorescent dye may be usually added to the water to make leaks easier to see. The test pressure may be considerably higher than the operating pressure to give a margin for safety, typically 150% of the design pressure. For example, a cylinder rated to DOT-2015 PSI may be tested at around 3360 PSI to ensure maximum usage and to provide more safety. Water may be commonly used because it is almost incompressible, and it may only expand by a very small amount in the event of an air cylinder rupture. If high pressure gas were used, then the gas may expand to several hundred times its compressed volume in an explosion, which may cause substantial damage and/or injury, including dismemberment and/or death.

During the process of being filled with compressed air to its rated pressure (e.g., 3000 to 4500 psi), an air cylinder may become over pressurized (e.g., filled to a pressure beyond its ability to maintain structural integrity). The air cylinder may possess a reduced capacity to maintain a rated pressure due to a manufacturing defect such as an air pocket, a scratch, a dent, and/or any other imperfection that may result in a stress concentrator and/or crack initiation site. Manufacturing defects may further include materials imperfections (e.g., improperly tempered metals, impurities that make a material more brittle and/or weaker, improperly bonded and/or formed composite structures, etc.). Air cylinders may further include damage due to improper maintenance, accidental impacts, water damage, temperature induced stress, oxidation, and radiation effects. For example, structures such as air cylinders that undergo significant changes in temperature may undergo thermal stresses as different parts of the structure expand and contract. Radiation damage may include degradation of a composite bonding material. Oxidation may include rusting of a steel structure. Composite structures may undergo other forms of chemical alteration that result in a weakened structure over time. In addition, metallic structures may have a limited fatigue-failure life cycle. An air cylinder may therefore also become weakened over time through the ordinary course of wear and tear associated with aging.

Once initiated, cracks may propagate rapidly under changing stresses, such as those that occur during a filling operation. Should a rupture occur, an explosion may include a rapid multidirectional expansion of gas. Parts of an air cylinder may form shrapnel in an explosion. In a sufficiently high energy event, sheet metal may be punctured by shrapnel, doors and hinges may open, uncertified locks may become broken, and/or a person near an air cylinder that is rupturing may become seriously injured.

The fill station (e.g., the fill site 102A-N) may therefore include the secure chamber (e.g., supply unit enclosure 500) that acts as a safety shield that confines a possible rupture of an over-pressurized breathable air apparatus (e.g., a SCBA air tank, etc.) within the secure chamber. The fill site 102 may be rated to withstand an explosively decompressing air cylinder that has ruptured, to restrict the flow of emerging gasses to prevent harm to any nearby persons and/or equipment, and to enclose any shrapnel that may be accelerated due to an explosion. The secure chamber (e.g., supply unit enclosure 500) may be an opening within the fill site 102 that allows filling to occur only when the structure has been closed and locked. In one or more embodiments, the fill site 102 may include a revolving structure to allow air cylinders to be mounted and unmounted while cylinders are filled within the locked secure chamber (e.g., supply unit enclosure 500) of the fill site 102. The revolving structure may include positions to mount two air cylinders at a time to be filled within the secure chamber. The locking mechanism 502 may secure the revolving platform on all sides to provide sufficient support that the revolving platform will not allow shrapnel to emerge in the event of an explosion. In one or more embodiments, the locking mechanism 502 may visually indicate that the revolving structure has been secured and supported around its perimeter when the lock has been engaged.

In addition, the revolving mechanism may allow the fill site 102 to maintain a constant pressure that fills an air tank within the secure chamber only when the locking mechanism has been engaged. In other words, unlocking the fill site 102 may allow the filled air bottles to be disconnected from the system without a danger that air pressure will continue to be maintained in the lines connected to pressurized bottles.

Therefore, once air pressure to the system has been raised to an appropriate level (e.g., 3000 psi, 4500 psi, etc.), an operator of the fill site 102 may add air to a cylinder by performing the steps of mounting an air cylinder to the fill station, rotating the revolving mechanism to enclose the air cylinder within the structure, and moving a lever to lock the station to allow air to flow into the air cylinders. The operator of the fill site may then move a lever to unlock the station, rotate the revolving mechanism to bring the air cylinder out from the enclosure, and unmount the filled air cylinder. Locking the fill site 102 may provide structural support to the revolving mechanism to prevent air and shrapnel from escaping in an explosion, and may provide a visual indicator that the perimeter of the opening around the revolving mechanism has been closed. The walls of the secure chamber may be made of a continuous material, welded, bolted, and/or attached in any other means required to sustain forces associated with an explosive venting of compressed gas. The secure chamber (e.g., supply unit enclosure 500) of the fill site 102 may also be required to meet a certification standard.

In an embodiment, a safety system of a structure may include a fill site system. A fill site system may include an apparatus that allows one or more firefighters to simultaneously refill an air tank of a Self Contained Breathing Apparatus (SCBA) unit while continuing to operate their breathing apparatus through the use of a specialized air connection (e.g., a rapid intervention company/crew (RIC) universal air connection (UAC), also described as the RIC/UAC coupling). The fill station may be a site (e.g., a location of a structure, a location within a building, etc.) to fill (e.g., supply, build up a level of, occupy the whole of, spread throughout, complete) a container with breathable air (e.g., compressed atmospheric gas meeting firefighting safety standards for quality and/or filtration) for emergency use. The specialized air connection may include a quick-connect system that allows the user to attach and/or detach the coupling without the use of a threaded connection.

In contrast, other methods and/or structures to refill an air tank of a SCBA unit may require a wearer to disconnect the air tank from the SCBA apparatus, connect the air tank to a mechanism to deliver compressed air into the air tank, and reinstall the air tank in the SCBA unit through a series of time consuming steps, during which the wearer of the SCBA unit may not have access to breathable air. The steps may involve screwing a connection together and unscrewing the connection using multiple turning actions. By allowing the wearer to continue to breathe while refilling an air tank of the SCBA unit, the wearer may avoid breathing excessive amounts of toxic, superheated and/or otherwise unbreathable air that may lead to immediate injury, long term health risks, unconsciousness, disablement, cancer, and/or death.

A SCBA unit may be a device worn by rescue workers, firefighters, industrial workers, and others to provide breathable air in a hostile environment. Areas in which the SCBA may be used for industrial purposes may include mining, petrochemical, chemical, and nuclear industries. The SCBA units designed for firefighting use may include components chosen for heat and flame resistance, which may add to a cost of manufacturing. Lighter materials may also be chosen to reduce the amount of effort needed by a firefighter to use the apparatus.

An open-circuit rescue or the firefighter SCBA may include a full-face mask, regulator, air cylinder, cylinder pressure gauge, and a harness with adjustable shoulder straps and waist belt that allows it be worn on a user's back. Air cylinders for the SCBA may be made of aluminium, steel, and/or of a composite construction (e.g., carbon-fiber wrapped). The composite cylinders may be the lightest in weight, which may make them preferred by fire departments. However, they may also have the shortest lifespan out of various types of air cylinders, and they may be taken out of service after 15 years. Air cylinders may further be required to undergo hydrostatic testing (e.g., every 3 years for composite cylinders, every 5 years for metal cylinders). The air cylinder may come in one of three standard sizes: 30, 45 or 60 minutes of breathing time. The relative fitness, and the level of exertion of the wearer, may often result in a variation of the actual usable time that the SCBA can provide air. Working time during which a firefighter is not exposed to toxic gasses may be reduced by 25% to 50% based on these factors.

The SCBA may use a negative and/or positive pressure system to deliver breathable air. A "negative pressure" SCBA may be used with a standard face mask instead of filter canisters, and air may be delivered when the wearer breathes in, or in other words, reduces the pressure in the mask to less than external air pressure. One disadvantage of this method may be that any leaks in the device or the interface between the mask and the face of the wearer could result in a reduction of the protection offered by the SCBA. The wearer may inhale small and/or large quantities of polluted and/or toxic gas through such leaks. A "positive pressure" SCBA may be set to maintain a small positive pressure inside a face mask. Although the pressure may drop when the wearer inhales, the positive pressure SCBA may continue to maintain a higher positive pressure than external air pressure within the mask. The positive pressure may cause any leak in the mask to result, the device always maintains a higher pressure inside the mask than outside of the mask. Thus, even if the mask leaks slightly, there may be a flow of clean air out of the device that prevents inward leakage of external air.

Some potential sources of a leak in the SCBA system may be hair that prevents a complete seal of a face mask, an overly large size of a face mask, a face mask wrinkle, a face mask puncture and/or tear, a degraded seal between face mask components. Other causes of a leak may include a temporary dislocation of the face mask, such as through an accidental collision with another firefighter and/or a wall, a fall by a fatigued and/or disoriented wearer, or falling debris and/or structural components of a burning building. A wearer of the face mask may also enter a darkened building where electrical power has failed and/or been interrupted or where smoke makes it difficult for the wearer to see, which may contribute to accidental collisions. A face mask may further be dislodged by a building occupant being assisted by a firefighter.

The use of a specialized air connection (e.g., a RIC/UAC fitting and/or coupling) may allow an SCBA unit user to avoid a risk associated with breathing toxic gasses while an air cylinder is refilled by filling the SCBA unit cylinder while it is still connected to the SCBA unit as an operational source of breathable air. The RIC/UAC fitting connected to the fill site 102 may therefore assist with expediting a breathable air extraction process from the air distribution system. The use of the specialized air connection may also avoid a risk of dislodging a user's mask and creating leaks in the SCBA system while the wearer refills an air cylinder. The specialized air connection may be a fitting designed to allow a direct transfer of air between fire fighters as a means of providing breathable air to a fire fighter without access to another means of refilling an air tank of an SCBA unit. The specialized air connection may further allow a fire fighter to provide air to a downed and/or disabled fire fighter who is unable to refill his own air tank. The specialized air connection may be a RIC/UAC coupling. The RIC/UAC coupling may allow two fire fighters with SCBA units to share their air regardless of manufacturer, after which the firefighters may have approximately equal levels of air. When a firefighter uses the RIC/UAC coupling to connect to another firefighter's SCBA unit, the pressure levels for each are balanced as air from an SCBA unit with more air flows to the connected SCBA unit.

A manufacturer of an SCBA unit may be required by the National Fire Protection Association (NFPA) 1981, the Standard on Open-Circuit Self-Contained Breathing Apparatus (SCBA) for Emergency Services, to build SCBA units that contain a RIC/UAC connection. The RIC/UAC coupling may be required for a newly manufactured SCBA unit to be in compliance for firefighting. The NFPA may be a U.S. organization that creates and maintains minimum standards and requirements for fire prevention and suppression activities, training, and equipment, as well as other life-safety codes and standards. This may include everything from building codes to the personal protective equipment utilized by firefighters while extinguishing a fire. State, local, and national governments may incorporate the standards and codes developed by the Association into their own law either directly or with only minor modifications. Even when not written into law, the Association's standards and codes may be accepted and recognized as a professional standard by a court of law.

NFPA 1981 may state in part that the RIC/UAC connection should allow a fully charged breathing air cylinder to connect to an SCBA unit of an entrapped and/or downed firefighter. The RIC/UAC coupling may be used in conjunction with a high pressure line. NFPA 1981 may further state that the pressurized air source should be able to provide 100 liters of air per minute using a RIC/UAC female fitting at a pressure compatible with the SCBA being used at an incident. The NFPA 1981 may also state that, for newly manufactured SCBA, the universal connection (RIC/UAC) should be permanently fixed to the unit within four inches of the threads of the SCBA cylinder valve.

The fill site 102 system may include variety of components to assist with expediting a breathable air extraction process from the air distribution system. For example, the fill site 102 system may include the supply unit 100 of a building structure to facilitate delivery of breathable air from a source of compressed air to the air distribution system 150 of the building structure. The fill site 102 may further include a valve to prevent leakage of the breathable air from the air distribution system 150 potentially leading to loss of system pressure. The fill site 102 system may further include a fill panel interior to the building structure having a RIC/UAC fitting pressure rated for a fill outlet of the fill panel to fill a breathable air apparatus to expedite a breathable air extraction process from the air distribution system 150 and to provide the breathable air to the breathable air apparatus at multiple locations of the building structure. The system may further include a distribution structure that is compatible with use with compressed air that facilitates dissemination of the breathable air of the source of compressed air to multiple locations of the building structure.

The valve to prevent leakage of the breathable air from the air distribution system 150 may be a part attached to a pipe and/or tube that controls the flow of a gas and/or a liquid. The valve may isolate the fill site 102 from the remainder of the fill site 102 system by preventing pressurized air from reaching the pressure gauge and the RIC/UAC fitting. Isolating the RIC/UAC fitting and pressure gauge may protect the parts from wear and/or possible damage due to fluctuating air pressures within the system. In addition, in the event of damage to and/or malfunction of the RIC/UAC fitting, pressure gauge and/or other connected parts, the valve may prevent the remainder of the system from venting gas through the damaged and/or malfunctioning part. The valve may be controlled by the turning knob placed in proximity to the pressure gauge to facilitate a control of the fill site 102 station by a firefighter under hazardous conditions. Some potential causes of damage to the fill site 102 may include a fire hazard, building damage, through a malfunction of a fire fighter's mating connection and/or SCBA unit.

In one or more embodiments, the fill panel (e.g., a control panel of the fill site, a flat, vertical, area where control and/or monitoring instruments are displayed) may include gauges to monitor system air pressure and fill pressure (e.g., as illustrated in FIG. 6). The valve to prevent leakage of the breathable air from the air distribution system 150 may be controlled by a knob mounted on the fill panel. The fill panel may include a hose that is connected to the RIC/UAC fitting (e.g., the fill hoses 622). The RIC/UAC fitting may be pressure rated (e.g., rated to 3000 psi, 4500 psi, etc.) for a fill outlet of the fill panel to fill a breathable air apparatus (e.g., a SCBA unit air cylinder, a SCUBA tank, etc.). The pressure rating may allow the RIC/UAC fitting to operate up to the rated pressure within a safety factor (e.g., 1.5, a multiple of the rated pressure) up to which the RIC/UAC fitting is designed and/or certified to operate.

As described above, the RIC/UAC fitting may expedite a breathable air extraction process from the air distribution system 150 and to provide the breathable air to the breathable air apparatus. The expedited breathable air extraction process may take place at multiple locations of the building structure (e.g., different floors, hallways, near emergency exits, etc.). These locations may be near typical points where fire fighters and emergency workers may encounter while searching a building that is on fire. These locations may also be near emergency exits where building occupants are likely to pass by on their way out of a building, where they may obtain access to breathable air either directly or with the assistance of a fire fighter.

In one or more embodiments, the system may further include a distribution structure that is compatible with use with compressed air that facilitates dissemination of the breathable air of the source of compressed air to multiple locations of the building structure. The distribution structure may include piping, pressure valves, and/or controls to regulate and/or direct pressurized air.

In one or more embodiments, the system may include the supply unit enclosure 500 that includes a weather resistant feature (e.g., to prevent lightning, wind, rain, and/or flooding damage, etc.). The system may include a supply unit enclosure 500 to prevent corrosion and/or physical damage (e.g., power surges in electronic components) caused by ultraviolet, infrared, and/or other types of solar radiation (e.g., using a metallic shield, using lead, and/or a chemical coating). The system may further include the locking mechanism 502 of the supply unit enclosure 500 (e.g., to prevent tampering, vandalism, and/or thieves.)

In one or more embodiments, the system may further include a fill panel enclosure (e.g., the fill site enclosure 624) to secure the fill panel from intrusions (e.g., due to falling building components, collisions with building occupants, etc.) that potentially compromise safety and reliability of the air distribution system. The supply unit enclosure 500 may be comprised of 18 gauge carbon steel that minimizes physical damage due to various hazards by protecting the supply unit 100 from intrusion and/or damage due to vehicle collisions, flooding, acid rain, snow, etc.

In one or more embodiments, the system may further include a valve of the supply unit 100 to perform any of a suspension of transfer and a reduction of flow of breathable air from the source of compressed air to the air distribution system 150 when useful. The valve of the supply unit 100 may therefore reduce a supply of air (e.g., an air pressure) to the distribution system when an excess pressure is provided by an external compressed air source. The valve of the supply unit 100 may cut off an incoming air supply that fails to meet required purity standards for fire fighters. The valve may also reduce an incoming air supply that is being vented through a leak and/or malfunctioning valve of the system to prevent a waste of a compressed air source.

In one or more embodiments, the system may further include a safety relief valve of any of the supply unit 100 and the fill panel set to have an open pressure of at most approximately 10% more than a design pressure of the air distribution system 150 to ensure reliability of the air distribution system through maintaining the system pressure such that it is within a threshold range of a pressure rating of each component of the air distribution system 150. The safety valve may prevent an overfilling of an air cylinder beyond its rated pressure capacity, which may cause the air cylinder to rupture. The safety valve may prevent a compressed air source from delivering air to hoses and/or fittings designed for lower pressures. The safety valve may prevent a rupture and/or other damage within the air delivery system caused by a spike in pressure. Some potential causes of a pressure spike may include a malfunctioning and/or improper pressure source, changes in temperature, and/or an explosion.

In one or more embodiments, the system may further include any Compressed Gas Association (CGA) connector and/or the RIC/UAC connector to ensure compatibility and to facilitate a connection of the supply unit 100 with a source of compressed air.

Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative rather than a restrictive sense.

What is claimed:

1. A method of safety of a mine structure, comprising:

expediting an air extraction process from an emergency support system by including a RIC (rapid interventions company/crew)/UAC (universal air connection) fitting to a fill panel to fill a breathable air apparatus;

ensuring that a prescribed pressure of the emergency support system maintains within a threshold range of the prescribed pressure by including a valve of the emergency support system to prevent leakage of breathable air from the emergency support system;

designating the prescribed pressure of the emergency support system based on an authority agency that specifies a pressure rating of the breathable air apparatus for a particular geographical location; and filling the breathable air apparatus at a fill site within the mine structure.

2. The method of claim 1 further comprising:

maintaining a prescribed pressure of the emergency support system such that a system pressure is compatible with the breathable air apparatus through a distribution structure that is rated for use with compressed air that couples a supply unit and the fill panel to transfer breathable air of a source of compressed air to the fill panel.

3. The method of claim 2 further comprising:

pressurizing breathable air to facilitate a flow of breathable air from the emergency support system to the breathable air apparatus.

4. The method of claim 3 further comprising:

pressurizing breathable air to increase a flow of breathable air to decrease an amount of time required to fill the breathable air apparatus.

5. A method of safety of a mine structure, comprising:

facilitating a flow of air from an emergency support system by including a RIC (rapid interventions company/crew) /UAC (universal air connection) fitting to a fill location to fill a breathable air apparatus;

ensuring that a prescribed pressure of the emergency support system maintains within a threshold range of the prescribed pressure by including a valve of the emergency support system to prevent leakage of breathable air from the emergency support system;

designating the prescribed pressure of the emergency support system based on an authority agency that specifies a pressure rating of the breathable air apparatus for a particular geographical location; and filling the breathable air apparatus at a fill site within the mine structure.

6. The method of claim 5 further comprising:

pressurizing breathable air to increase the flow of breathable air to decrease an amount of time required to fill the breathable air apparatus.

7. The method of claim 6 further comprising:

connecting the RIC/UAC fitting to a fill station to provide an additional source of breathable air.

8. The method of claim 7 wherein:

the fill location is a site in the mine structure providing access to the RIC/UAC fitting coupled to the emergency support system.

9. The method of claim 8 further comprising:

adjusting a fill pressure to ensure that the fill pressure of the source of compressed air does not exceed the prescribed pressure of the emergency support system through a pressure regulator of the supply unit.

10. A method of safety of a mine structure, comprising:

extracting breathable air from an emergency support system by including a RIC (rapid interventions company/crew) /UAC (universal air connection) fitting to a fill location to fill a breathable air apparatus, ensuring that a prescribed pressure of the emergency support system maintains within a threshold range of the prescribed pressure by including a valve of the emergency support system to prevent leakage of breathable air from the emergency support system;

designating the prescribed pressure of the emergency support system based on an authority agency that specifies a pressure rating of the breathable air apparatus for a particular geographical location; and filling the breathable air apparatus at a fill site within the mine structure.

11. The method of claim 10 further comprising:

pressurizing the breathable air in the emergency support system to a pressure greater than a pressure rating of the breathable air apparatus.

12. The method of claim 11 further comprising:

adjusting a pressure of the RIC/UAC fitting by including a valve of the emergency support system to match with a threshold range the pressure rating of the breathable air apparatus.

13. The method of claim 12 further comprising:

suspending transfer of breathable air from the source of compressed air to the emergency support system through utilizing a valve of the supply unit when necessary.

14. The method of claim 13 further comprising:

preventing leakage of air from the emergency support system potentially leading to pressure loss of the emergency support system through utilizing a valve of the fill panel.

15. A method of safety of a mine structure, comprising:

safeguarding a filling process of a breathable air apparatus by enclosing the breathable air apparatus in a secure chamber of a fill site of the emergency support system of the mine structure to provide a safe placement to supply the breathable air to the breathable air apparatus;

ensuring that a prescribed pressure of the emergency support system maintains within a threshold range of the prescribed pressure by including a valve of the emergency support system to prevent leakage of breathable air from the emergency support system;

designating the prescribed pressure of the emergency support system based on an authority agency that specifies a pressure rating of the breathable air apparatus for a particular geographical location; and filling the breathable air apparatus at a fill site within the mine structure.

16. The method of claim 15 further comprising:

maintaining the prescribed pressure of the emergency support system such that a system pressure is compatible with a breathable air apparatus through a distribution structure that is rated for use with compressed air that couples a supply unit and the fill site to transfer breathable air of a source of compressed air to the fill site.

17. The method of claim 16 further comprising:

securing the breathable air apparatus to prevent the breathable air apparatus from injuring a user of the breathable air apparatus during the filling process of a breathable air apparatus.

18. The method of claim 17 further comprising:

securing the breathable air apparatus to ensure that the breathable air apparatus has access to air during the filling process.

19. A method of safety of a mine structure, comprising:

safeguarding a filling process of a breathable air apparatus by enclosing the breathable air apparatus in a secure device of a fill site of the emergency support system of the mine structure to provide a safe placement to supply the breathable air to the breathable air apparatus;

ensuring that a prescribed pressure of the emergency support system maintains within a threshold range of the prescribed pressure by including a valve of the emergency support system to prevent leakage of breathable air from the emergency support system;

designating the prescribed pressure of the emergency support system based on an authority agency that specifies a pressure rating of the breathable air apparatus for a particular geographical location; and filling the breathable air apparatus at a fill site within the mine structure.

20. The method of claim 19 further comprising:

securing the breathable air apparatus to prevent the breathable air apparatus from injuring a user of the breathable air apparatus during the filling process of a breathable air apparatus.

21. The method of claim 20 further comprising:

securing the breathable air apparatus to ensure that the breathable air apparatus has access to air during the filling process.

22. The method of claim 21 wherein:

the secure device prevents the escape of the breathable air apparatus in case the breathable air apparatus is damaged during the filling process of the breathable air apparatus.

23. The method of claim 22 further comprising:

adjusting a fill pressure to ensure that the fill pressure of the source of compressed air does not exceed the prescribed pressure of the emergency support system through a pressure regulator of the supply unit.

* * * * *